United States Patent
Lipkens et al.

(10) Patent No.: US 11,381,922 B2
(45) Date of Patent: *Jul. 5, 2022

(54) ACOUSTIC TRANSDUCER DRIVER AND CONTROLLER

(71) Applicant: FloDesign Sonics, Inc., West Springfield, MA (US)

(72) Inventors: Bart Lipkens, Bloomfield, CT (US); Ronald Musiak, Westfield, MA (US); John Artis, Santa Rosa, CA (US)

(73) Assignee: FloDesign Sonics, Inc., West Springfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/943,303

(22) Filed: Jul. 30, 2020

(65) Prior Publication Data
US 2020/0359136 A1 Nov. 12, 2020

Related U.S. Application Data

(63) Continuation of application No. 16/221,283, filed on Dec. 14, 2018, now Pat. No. 10,785,574.
(Continued)

(51) Int. Cl.
*H04R 9/06* (2006.01)
*H04R 1/28* (2006.01)
(Continued)

(52) U.S. Cl.
CPC ............ *H04R 9/063* (2013.01); *B01D 17/04* (2013.01); *B01D 21/28* (2013.01); *B06B 1/0261* (2013.01);
(Continued)

(58) Field of Classification Search
CPC . H04R 3/00; H04R 3/002; H04R 3/04; H04R 9/063; H04R 1/2807; H03G 3/20;
(Continued)

(56) References Cited

U.S. PATENT DOCUMENTS 3,555,311 A 1/1971 Weber
3,948,489 A 4/1976 Sawyer
(Continued)

FOREIGN PATENT DOCUMENTS

CN 201026489 Y 2/2008
CN 104722106 A 6/2015
(Continued)

OTHER PUBLICATIONS

Design of Harmonies—Caused thermal Overload protection for AC Filter Reactor and its Application in HVDC power Transmission projects, Power system technology , vol. 23, No. 2, 2013, pp. 482-487.
(Continued)

*Primary Examiner* — William A Jerez Lora
(74) *Attorney, Agent, or Firm* — FloDesign Sonics, Inc.

(57) ABSTRACT

An acoustophoretic system is controlled and driven to attain a desired level of performance. An RF controller and a driver provide a frequency and power to an acoustic transducer, which can be implemented as a piezoelectric element, which presents a reactive load or a complex load. A controller implements a control technique for efficient transducer operation. The control technique can locate a frequency for operation that is at a reactance minimum or maximum for the system to produce a modal pattern and to provide efficient operation of the transducer. A method of detecting a minimum or maximum reactance in a acoustophoretic system used to trap, separate, deflect, cluster, fractionate or otherwise process particles or secondary fluids or tertiary fluids in a primary fluid and utilizing the frequency of the detected reactance to operate the acoustophoretic system.

19 Claims, 38 Drawing Sheets

Related U.S. Application Data

(60) Provisional application No. 62/614,354, filed on Jan. 5, 2018, provisional application No. 62/599,017, filed on Dec. 14, 2017.

(51) Int. Cl.
  *B01D 17/04* (2006.01)
  *B06B 1/02* (2006.01)
  *B01D 21/28* (2006.01)

(52) U.S. Cl.
  CPC ........ *H04R 1/2807* (2013.01); *B06B 2201/70* (2013.01)

(58) Field of Classification Search
  CPC ..... H03F 1/34; B06B 2201/70; B06B 1/0261; B01D 17/04; B01D 21/28
  USPC ............................ 381/89, 95, 96, 108, 121
  See application file for complete search history.

(56) References Cited

U.S. PATENT DOCUMENTS

| | | |
|---|---|---|
| 4,048,454 A | 9/1977 | Barcus et al. |
| 4,264,003 A | 4/1981 | Gill |
| 4,320,659 A | 3/1982 | Lynnworth et al. |
| 4,398,325 A | 8/1983 | Piaget et al. |
| 4,673,512 A | 6/1987 | Schram |
| 4,743,361 A | 5/1988 | Schram |
| 4,759,775 A | 7/1988 | Peterson et al. |
| 4,821,838 A | 4/1989 | Chen |
| 4,823,042 A | 4/1989 | Coffey et al. |
| 4,836,684 A | 6/1989 | Javorik et al. |
| 4,877,516 A | 10/1989 | Schram |
| 4,878,210 A | 10/1989 | Mitome |
| 5,085,783 A | 2/1992 | Feke et al. |
| 5,225,089 A | 7/1993 | Benes et al. |
| 5,371,429 A | 12/1994 | Manna |
| 5,415,175 A | 5/1995 | Hanafy et al. |
| 5,527,460 A | 6/1996 | Trampler et al. |
| 5,562,823 A | 10/1996 | Reeves |
| 5,626,767 A | 5/1997 | Trampler et al. |
| 5,665,605 A | 9/1997 | Coakley et al. |
| 5,688,405 A | 11/1997 | Dickinson et al. |
| 5,831,166 A | 11/1998 | Kozuka et al. |
| 5,902,489 A | 5/1999 | Yasuda et al. |
| 5,951,456 A | 9/1999 | Scott |
| 6,106,590 A | 8/2000 | Ueno et al. |
| 6,216,538 B1 | 4/2001 | Yasuda et al. |
| 6,273,262 B1 | 8/2001 | Yasuda et al. |
| 6,326,213 B1 | 12/2001 | Letcher et al. |
| 6,332,541 B1 | 12/2001 | Coakley et al. |
| 6,467,350 B1 | 10/2002 | Kaduchak et al. |
| 6,482,327 B1 | 11/2002 | Mori et al. |
| 6,699,711 B1 | 3/2004 | Hahn et al. |
| 6,936,151 B1 | 8/2005 | Lock et al. |
| 9,663,756 B1 | 5/2017 | Lipkens et al. |
| 10,428,324 B1 | 10/2019 | Coons et al. |
| 2001/0015211 A1 | 8/2001 | Schuler et al. |
| 2004/0047477 A1 | 3/2004 | Bank et al. |
| 2004/0057866 A1 | 3/2004 | Zumeris et al. |
| 2004/0065599 A1 | 4/2004 | Lal et al. |
| 2004/0069708 A1 | 4/2004 | Laurell et al. |
| 2004/0112841 A1 | 6/2004 | Scott |
| 2004/0113522 A1 | 6/2004 | Nagahara et al. |
| 2006/0037915 A1 | 2/2006 | Strand et al. |
| 2006/0037916 A1 | 2/2006 | Trampler |
| 2006/0124555 A1 | 6/2006 | Nakatani |
| 2006/0223185 A1 | 10/2006 | Fedorov et al. |
| 2007/0267351 A1 | 11/2007 | Roach et al. |
| 2007/0272618 A1 | 11/2007 | Gou et al. |
| 2008/0053787 A1 | 3/2008 | Bagajewicz |
| 2008/0156737 A1 | 7/2008 | Janssen et al. |
| 2008/0181828 A1 | 7/2008 | Kluck |
| 2008/0217259 A1 | 9/2008 | Siversson |
| 2009/0029870 A1 | 1/2009 | Ward et al. |
| 2009/0036912 A1 | 2/2009 | Wiener et al. |
| 2009/0107241 A1 | 4/2009 | Goddard et al. |
| 2009/0226994 A1 | 9/2009 | Lemor et al. |
| 2009/0295505 A1 | 12/2009 | Mohammadi et al. |
| 2010/0078384 A1 | 4/2010 | Yang |
| 2010/0126922 A1 | 5/2010 | Takahashi et al. |
| 2010/0139377 A1 | 6/2010 | Huang et al. |
| 2010/0143879 A1 | 6/2010 | Curran |
| 2010/0206818 A1 | 8/2010 | Leong et al. |
| 2010/0255573 A1 | 10/2010 | Bond et al. |
| 2010/0331869 A1 | 12/2010 | Voegele et al. |
| 2011/0123392 A1 | 5/2011 | Dionne et al. |
| 2011/0154890 A1 | 6/2011 | Holm et al. |
| 2011/0166551 A1 | 7/2011 | Schafer |
| 2011/0262990 A1 | 10/2011 | Wang et al. |
| 2011/0278218 A1 | 11/2011 | Dionne et al. |
| 2011/0284475 A1 | 11/2011 | Kolodny |
| 2012/0034396 A1 | 2/2012 | Raeymaekers et al. |
| 2012/0132071 A1 | 5/2012 | Kusuura |
| 2012/0149126 A1 | 6/2012 | Wilson et al. |
| 2012/0160746 A1 | 6/2012 | Thorslund et al. |
| 2012/0267288 A1 | 10/2012 | Chen et al. |
| 2013/0175226 A1 | 7/2013 | Coussios et al. |
| 2013/0192958 A1 | 8/2013 | Ding et al. |
| 2013/0277316 A1 | 10/2013 | Dutra et al. |
| 2013/0284271 A1 | 10/2013 | Lipkens et al. |
| 2014/0033808 A1 | 2/2014 | Ding et al. |
| 2014/0036632 A1 | 2/2014 | Suyama |
| 2014/0047909 A1 | 2/2014 | Fernald et al. |
| 2014/0175946 A1 | 6/2014 | Wischnewskiy |
| 2014/0193381 A1 | 7/2014 | Warner et al. |
| 2014/0230912 A1 | 8/2014 | Aider et al. |
| 2014/0261535 A1 | 9/2014 | Stumpf |
| 2014/0301902 A1 | 10/2014 | Fernald et al. |
| 2014/0319077 A1 | 10/2014 | Lipkens et al. |
| 2014/0377834 A1 | 12/2014 | Presz et al. |
| 2015/0001388 A1 | 1/2015 | Morris et al. |
| 2015/0056715 A1 | 2/2015 | Laugham et al. |
| 2015/0125948 A1 | 5/2015 | Lipkens et al. |
| 2015/0148712 A1 | 5/2015 | Loven et al. |
| 2015/0191716 A1 | 7/2015 | Lipkens et al. |
| 2015/0204993 A1 | 7/2015 | Leggett et al. |
| 2015/0209696 A1 | 7/2015 | Kambayashi et al. |
| 2015/0321129 A1 | 11/2015 | Lipkens et al. |
| 2016/0008532 A1 | 1/2016 | Fiering et al. |
| 2016/0089620 A1 | 3/2016 | Lipkens et al. |
| 2016/0142832 A1* | 5/2016 | Hillbratt ............ A61N 1/0541 |
| | | 381/317 |
| 2016/0153249 A1 | 6/2016 | Mitri |
| 2016/0181505 A1 | 6/2016 | Karrai et al. |
| 2016/0184790 A1 | 6/2016 | Sinha et al. |
| 2016/0237110 A1 | 8/2016 | Gilmanshin et al. |
| 2016/0279540 A1 | 9/2016 | Presz et al. |
| 2016/0287778 A1 | 10/2016 | Leach et al. |
| 2016/0312168 A1 | 10/2016 | Pizzi |
| 2016/0319270 A1 | 11/2016 | Lipkens et al. |
| 2016/0325206 A1 | 11/2016 | Presz et al. |
| 2016/0332159 A1 | 11/2016 | Dual et al. |
| 2016/0336877 A1 | 11/2016 | Wischnewskiy et al. |
| 2016/0339360 A1 | 11/2016 | Lipkens et al. |
| 2016/0363579 A1 | 12/2016 | Gilmanshin et al. |
| 2017/0000516 A1 | 1/2017 | Stulen et al. |
| 2017/0002839 A1 | 1/2017 | Bukland et al. |
| 2017/0029802 A1 | 2/2017 | Lipkens et al. |
| 2017/0052174 A1 | 2/2017 | Branch et al. |
| 2017/0062187 A1* | 3/2017 | Radomski ......... H01J 37/32155 |
| 2017/0066061 A1* | 3/2017 | Short ................. B23B 31/1179 |
| 2017/0080423 A1 | 3/2017 | Dauson et al. |
| 2017/0139001 A1* | 5/2017 | Lindell .............. G01R 19/0092 |
| 2017/0175509 A1 | 6/2017 | Abdel-Fattah et al. |
| 2017/0214339 A1 | 7/2017 | Wischnewskiy et al. |
| 2017/0291122 A1* | 10/2017 | Lipkens .................... B06B 1/06 |
| 2017/0321208 A1 | 11/2017 | Lipkens et al. |
| 2017/0354901 A1 | 12/2017 | Collins et al. |
| 2018/0003110 A1 | 1/2018 | Lipkens et al. |
| 2018/0027630 A1* | 1/2018 | DeJonge ................ H05B 45/10 |
| | | 315/86 |
| 2018/0043473 A1 | 2/2018 | Helvajian et al. |

(56) References Cited

U.S. PATENT DOCUMENTS

| | | | |
|---|---|---|---|
| 2018/0052095 A1 | 2/2018 | Cumbo et al. | |
| 2018/0055529 A1 | 3/2018 | Messerly et al. | |
| 2018/0071981 A1 | 3/2018 | Collino et al. | |
| 2018/0088083 A1 | 3/2018 | Sinha et al. | |
| 2018/0095067 A1 | 4/2018 | Huff et al. | |
| 2018/0157107 A1 | 6/2018 | Koyama et al. | |
| 2018/0177490 A1 | 6/2018 | Shiraishi | |
| 2018/0186107 A1 | 7/2018 | Buchanan | |
| 2018/0257076 A1 | 9/2018 | Weitz et al. | |
| 2018/0296954 A1 | 10/2018 | Trampler et al. | |
| 2018/0334697 A1 | 11/2018 | Shachar et al. | |
| 2018/0369816 A1 | 12/2018 | Ai et al. | |
| 2019/0070528 A1 | 3/2019 | Luthe et al. | |
| 2019/0091683 A1 | 3/2019 | Baudoin et al. | |
| 2019/0107420 A1 | 4/2019 | Kincel | |
| 2019/0160463 A1 | 5/2019 | Ai et al. | |
| 2019/0246912 A1 | 8/2019 | Bahmanyar et al. | |
| 2020/0064418 A1 | 2/2020 | Gregg et al. | |
| 2020/0095972 A1* | 3/2020 | Tona | F03B 15/00 |
| 2020/0284717 A1 | 9/2020 | Ishimaru | |
| 2020/0316586 A1 | 10/2020 | Riaud et al. | |
| 2020/0384463 A1 | 12/2020 | Davis et al. | |

FOREIGN PATENT DOCUMENTS

| | | |
|---|---|---|
| CN | 104785429 A | 7/2015 |
| CN | 105181794 A | 12/2015 |
| CN | 105307099 A | 2/2016 |
| CN | 107071684 A | 8/2017 |
| EP | 2882091 A1 | 6/2015 |
| EP | 3323444 A1 | 5/2018 |
| JP | 2-290266 A | 11/1990 |
| JP | 9-136090 A | 5/1997 |
| JP | 2001-212514 A | 8/2001 |
| JP | 2005-349267 A | 12/2005 |
| JP | 2014-175807 A | 9/2014 |
| JP | 2017-515669 A | 6/2017 |
| RU | 2037327 C1 | 6/1995 |
| RU | 2085933 C1 | 7/1997 |
| WO | 00/41794 A1 | 7/2000 |
| WO | 2011/027146 A2 | 3/2011 |
| WO | 2013/043044 A1 | 3/2013 |
| WO | 2013/043046 A1 | 3/2013 |
| WO | 2013138797 A1 | 9/2013 |
| WO | 2014/029505 A1 | 2/2014 |
| WO | 2015/144135 A1 | 10/2015 |
| WO | 2016/124542 A1 | 8/2016 |
| WO | 2018/034655 A1 | 2/2018 |
| WO | 2018/038711 A1 | 3/2018 |

OTHER PUBLICATIONS

European Search Report received for European Patent Application No. 18887565.2 dated Aug. 12, 2021, 10 pages.

International Search Report and Written Opinion for International Application No. PCT/US2018/065839, dated May 16, 2019, 11 pages.

Augustsson et al., "Acoustofluidics 11: Affinity specific extraction and sample decomplexing using continuous flow acoustophoresis", Lab on the Chip, vol. 12 No. 10, 2012, pp. 1742-1752.

Augustsson et al., "Acoustophoretic Microfluidic Chip For Sequential Elution Of Surface Bound Molecules From Beads Or Cells", Biomicrofluidics, vol. 6, American Institute of Physics, 2012, 10 pages.

Ding et al., "Cell Separation Using Tilted-angle Standing Surface Acoustic Waves", PNAS Early Edition, 2014, 6 pages.

Ding et al., "Tunable patterning of microparticles and cells using standing surface acoustic waves", Lab on a Chip, Issue 12, 2012, pp. 2491-2497.

Gallego-Juarez et al., "Piezoelectric ceramics and ultrasonic transducers", Journal of Physics E: Scientific Instruments, 1989, pp. 804-816.

Grinenko et al., "Efficient Counter-propagating Wave Acoustic Micro-particle Manipulation", Applied Physics Letters, vol. 101 (233501), 2012, 4 pages.

Hammarstrom et al., "Seed Particle-enabled Acoustic Trapping Of Bacteria And Nanoparticles In Continuous Flow Systems", Lab on a Chip, vol. 12, 2012, pp. 4296-4304.

Lee et al., "Nonviral Transfection of Suspension Cells in Ultrasound Standing Wave Fields", Ultrasound in Medicine & Biology, vol. 33 No. 5., 2007, pp. 734-742.

Lilliehorn et al., "Trapping of microparticles in the near field of an ultrasonic transducer", Ultrasonics, vol. 43, 2005, pp. 293-303.

Reslan et al., "Transfection of Cells in Suspension by Ultrasound Cavitation", Journal Of Controlled Release, Elsevier, Amsterdam, NL, vol. 142, No. 2, Mar. 3, 2010, pp. 251-258.

Son et al., "Input impedance matching of acoustic transducers operating at off-resonant frequencies", IEEE Transactions on Ultrasonics, Ferroelectrics, and Frequency Control, vol. 57, No. 12, Dec. 2010, pp. 2784-2794.

Wang et al., "Aptamer-conjugated and drug-loaded acoustic droplets for ultrasound theranosis", Biomaterials, vol. 33, Issue 6, Feb. 2012, pp. 1939-1947.

Wang et al., "Recent advances in particle and droplet manipulation for lab-on-a-chip devices based on surface acoustic waves", Lab on a Chip, vol. 11, 2011, pp. 1280-1285.

Woodside et al., "Measurement of Ultrasonic Forces for Particle-Liquid Separations", AIChE Journal, vol. 43, No. 7, Jul. 1997, pp. 1727-1736.

* cited by examiner

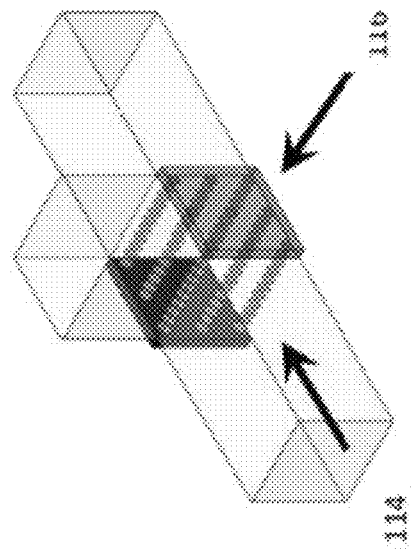
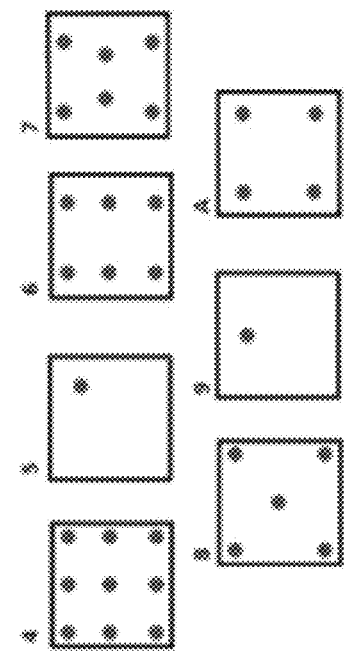
Figure 8A
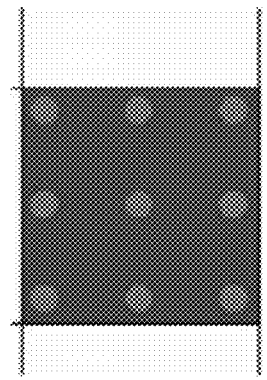
Figure 8B
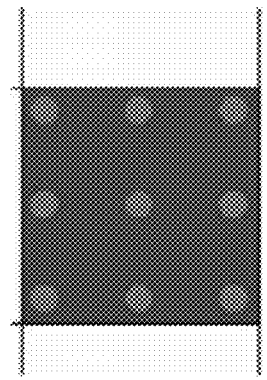
Figure 8C
Figure 8D Global frequency sweep to search for Anti-Resonance location Perform global sweep to locate the reactance minimum desired Frequency mini-sweep details

ACOUSTIC TRANSDUCER DRIVER AND CONTROLLER

CROSS-REFERENCE TO RELATED APPLICATIONS

This application is a Continuation application of U.S. application Ser. No. 16/221,283, filed Dec. 14, 2018, which claims the benefit of U.S. Provisional Application Ser. No. 62/614,354, filed Jan. 5, 2018, and U.S. Provisional Application Ser. No. 62/599,017, filed Dec. 14, 2017, the entire contents of which are hereby incorporated herein by reference.

BACKGROUND

Acoustophoresis is the use of acoustics to perform separation of materials. For example, particles and secondary fluids can be separated from a primary or host fluid using acoustic standing waves. Acoustic standing waves can exert forces on particles in a fluid when there is a differential in density and/or compressibility, otherwise known as the acoustic contrast factor. The pressure profile in a standing wave contains areas of local minimum pressure amplitudes at standing wave nodes and local maxima at standing wave anti-nodes. Depending on their density and compressibility, the particles can be trapped at the nodes or anti-nodes of the standing wave. Generally, the higher the frequency of the standing wave, the smaller the particles that can be trapped.

At a micro scale, for example with structure dimensions on the order of micrometers, conventional acoustophoresis systems tend to use half or quarter wavelength acoustic chambers, which at frequencies of a few megahertz are typically less than a millimeter in thickness, and operate at very slow flow rates (e.g., µL/min). Such systems are not scalable since they benefit from extremely low Reynolds number, laminar flow operation, and minimal fluid dynamic optimization.

At the macro-scale, planar acoustic standing waves have been used in separation processes. However, a single planar wave tends to trap the particles or secondary fluid such that separation from the primary fluid is achieved by turning off or removing the planar standing wave. The removal of the planar standing wave may hinder continuous operation. Also, the amount of power that is used to generate the acoustic planar standing wave tends to heat the primary fluid through waste energy, which may be disadvantageous for the material being processed.

SUMMARY

An electrical source, which may include an oscillator and an amplifier, may be utilized to perturb a piezoelectric material that may be utilized to generate acoustic waves. When a reflector is utilized in conjunction with the piezoelectric material, the acoustic waves that are generated may be reflected back to the piezoelectric material to form an acoustic standing wave. The acoustic standing wave is comprised of nodes and anti-nodes that allow for pressure differentials in the media where the acoustic standing wave is generated.

Fine-tuning of the perturbation of the piezoelectric material and reaction to the reflected wave in the acoustic standing wave can improve the utilization of the nodes and anti-nodes in the acoustic standing wave. The acoustic standing wave can be used for processing materials and fluids within a primary fluid.

A control system is provided that can respond to the properties of the acoustic standing wave. The control system can regulate the acoustic standing wave to achieve trapping, separation, segregation, characterization, deflection and categorization, among other processes, of particles and secondary fluids within a primary fluid. The results of the application of acoustophoresis using the control system are applicable in cell and gene therapy, as well as clarification techniques. The applications available are myriad, and may be used in fields including energy (oil, gas, biofuels), biopharma (e.g. manufacture of therapeutics), food industries, bioagriculture, to name a few.

In one example implementation, an electronic control is operated according to a control scheme to drive the electronics that perturbs a piezoelectric material in a manner to form an acoustic standing wave between the piezoelectric material and a reflector. The acoustic standing wave may be formed through the use of a single piezoelectric material that perturbs a secondary material such that it forms an acoustic standing wave within the secondary material and any channels that are within the secondary material.

Acoustic standing waves may be utilized to trap, deflect, separate, and/or segregate particles and/or secondary fluids that are in a primary fluid. Typically, the acoustic standing wave is set at a certain frequency that allows for trapping of specific particles or secondary fluids. As the acoustic standing wave traps particles and/or secondary fluids, the physical characteristics of the acoustic standing wave change and the control used to drive the piezoelectric material is operated to compensate for the changes. The compensation for changes within the acoustic standing wave at a frequency of, for example, 2 MHz uses a fast and timely feedback of the physical properties of the acoustic standing wave, as seen by the piezoelectric material, such that the control system responds to the changes in the acoustic standing wave. The speed of the feedback can be sufficient to reduce or eliminate aliasing in the response to the physical changes that are happening within the acoustic standing wave. This feedback and overall closed loop speed avoids receiving incorrect feedback for compensation of the physical changes that are occurring in the acoustic standing wave.

The separation of materials with the use of an acoustic standing wave is a process called acoustophoresis. The tuning of the acoustic standing wave to improve or optimize the separation of the particles or secondary fluid or tertiary fluid in a primary fluid contributes to improving the efficiency of the acoustophoresis process and/or reducing or minimizing the energy input into the acoustic standing wave system.

A process of tracking the reactance of the piezoelectric material can be used to control the acoustic standing wave as it collects particles or secondary fluids or tertiary fluids at the pressure nodes and/or anti-nodes of the acoustic standing wave. The collection of the materials depends on the size and the acoustic contrast factor of the particles or secondary fluids or tertiary fluids to the primary fluid. The reactance tracking permits the acoustic standing wave to be controlled to improve or optimize efficiency of material collection, as well as permitting rapid adjustments to the control in response to a number of factors, including the amount of material that is held in the acoustic standing wave.

The acoustic standing wave may be a single, planar wave, a multidimensional acoustic standing wave or a combination of both. The piezoelectric material may be driven to obtain superimposed or superpositioned frequency modes on each other.

The finding of the minimum reactance point, known as Xmin, is accomplished through a series of fast sweeps of frequency of the drive signal applied to the piezoelectric material to detect and correct for changes in resistance and reactance during operation. The minimum reactance Xmin, or frequencies related to Xmin, can be used as an operating setpoint to seek to optimize performance.

Discussed herein are systems and methods for acoustophoresis for generating improved or optimized acoustic radiation force fields to improve separation and/or collection efficiency.

Control of the acoustic transducer can be implemented on the basis of power setpoints. For example, a user can set a desired power level for power delivered to the transducer. Performance of acoustophoresis in an acoustic chamber using the acoustic transducer can be modulated on the basis of modulated input power to the acoustic transducer. In some instances, a power setpoint is desired for operation, while other parameters, such as frequency, for example, are modified. The power setpoint determines the power output of an RF power supply or power amplifier. A power control is provided to maintain the power setpoint, while other parameters associated with operation of the acoustophoresis device are varied. The power control senses signals provided to the acoustic transducer, such as, for example, voltage and current. These feedback signals are used to determine frequency and phase angle for the power delivered to the transducer. In some examples, a buck converter is used as the power supply. The buck converter has a response bandwidth, which may influence the responsiveness of the power control. For example, if the buck converter bandwidth is relatively narrow, the system response for the power control may be relatively slow for the desired operational performance environment for the acoustophoresis device. The system may be controlled in a similar manner using: apparent power, reactive power, root mean square of the voltage, root mean square of the current. The system may also be driven with a constant buck voltage.

A number of different materials at a range of concentrations may be processed through the acoustophoresis device, each of which may provide different load characteristics on the acoustic transducer and acoustic chamber. The power supply thus may be subjected to a wide range of loads, which may place demands on the power supply that are challenging to meet. For example, heavy loading of the acoustic transducer and/or acoustic chamber experienced with certain types of materials and/or concentrations being processed may cause power supply components to be overloaded, and/or overheated, or may cause trip point thresholds to be met or exceeded. The heavy loading or trip point thresholds crossings may cause faults to be identified in the power control, causing the power supply and/or the drive signal to be shut down. In addition, the power demands on the power supply may change significantly with changes in other operational parameters, such as temperature, frequency or loading characteristics, including reactance. Power control based on a desired power levels the point may thus imply other operational setpoints, such as frequency, to manage operation of the power supply and acoustophoresis device to handle a range of loads.

In some implementations, an RF linear amplifier is used to supply power to the transducer. The linear amplifier may operate by receiving an input signal, which may be AC or DC, and amplifying the input signal in accordance with the operational characteristics of the linear amplifier. Linear amplifiers are typically designed to have a linear response, such that any input signal is amplified by the same gain, within the operating parameters or specifications of the linear amplifier. This linear operation can be achieved through the use of techniques that contribute to linearizing the response of the linear amplifier, potentially in areas where non-ideal conditions tend to impose nonlinearities on the response. However, linear operation is attained at the cost of power regulation, usually generating significant heat losses as well as incurring inefficient operation. Accordingly, linear amplifiers tend to consume significant amounts of power, even when the magnitude of the input signal is relatively small and/or when the gain is relatively small. When demands are placed on the linear amplifier to supply power in response to changing system conditions, such as frequency or loading, challenges are presented in terms of responsiveness and avoiding overloads.

In addition, linear amplifiers are designed for nominal applications, for example, where a 50 ohm load is specified. The load applied to the linear amplifier is thus intended to be composed of mostly real impedance, or resistance, and tolerates a relatively small amount of reactive impedance. In the case of providing power to an acoustic transducer that is composed of a piezoelectric material, the power supply sees a highly reactive load, which limits the usefulness of an RF linear amplifier as the power supply.

The PZT-chamber system presents to an electronic signal source (driver) a range of electrical, driving-point impedances from purely real to purely reactive and anything in between based on the operating conditions in that system. Controlling processes in the acoustic chamber based on the driving-point impedance presented to the driver by the system is also part of this embodiment. Different processes present different driving-point impedances.

The piezoelectric material may be driven with a current source or a voltage source. The current source may permit greater electro-mechanical freedom in supporting and sustaining desirable vibratory modes in the piezoelectric material. A drive and control scheme can be provided to generate a low harmonic signal into the piezoelectric material. The control of the acoustic transducer that generates the acoustic standing wave in the fluid medium can utilize a feedback loop and a computational processor. An inductor-capacitor-inductor (LCL) circuit configuration may be used to generate a low harmonic function wave, such as a sine wave, into the piezoelectric material. The low harmonic sine wave permits less parasitic vibrations of the piezoelectric material. Such a sine wave may also permit the piezoelectric material to generate less heat when it vibrates.

An LCL configuration can act on the signal from the amplifier as a filter to reduce the harmonic content of the amplifier output. The LCL may thus act, at least in part, as a low pass filter for the amplifier output. In some examples, the LCL may cause the amplifier output to be filtered to a pure sine wave form. As a result, the perturbation of the piezoelectric material does not generate extra, parasitic vibrations of the material. The output inductor of the LCL structure provides a current source drive to the piezoelectric material. The LCL input, and thus the current source, is controlled to improve the piezoelectric material's performance in generating an acoustic wave.

The acoustic transducer can be driven to create a multi-dimensional acoustic standing wave in a coupled medium, where the wave has at least non-zero acoustic forces in a direction transverse to the propagation direction of the wave. The multi-dimensional acoustic standing wave generation process takes advantage of the higher-order vibratory modes of a loosely suspended piezoelectric plate.

Piezoelectric material changes shape based on an electrical signal applied to it, such as a voltage or current signal, or based on a corresponding electric field permeating the material. The electric field from external charges affects the fields of the bound charges in the material and thereby affects the shape of the material. The electrical signal can be from a voltage source. In that case the amount of material deformation is related to the voltage applied. For example, the deformation may be 'voltage clamped' or 'voltage damped'. The amount of charge induced is related to the applied voltage and the properties of the material. This relationship can be expressed mathematically as $Q=C*V$, where Q is charge, C is material capacitance, and V is the voltage of the applied signal. Electrodes may be attached to the piezoelectric material to provide a conduit for the applied signal. In that case the voltage, and the corresponding electric field, is a function of the externally applied charges. Using the above equation, the voltage can be express as $V=Q/C$. The resultant voltage may be 'unconstrained' in relation to operation of the piezoelectric device. The 'C' of the piezoelectric device is due to its physical geometry and material properties. Since the material changes shape as a function of the electric field permeating it, the 'C' of the device is a function of the electric field permeating it. For a given Q, and driving the material with a current source that is a time varying source of charge, C changes as a function of electric field, which changes the voltage across the device to 'accommodate' the changed C. In a voltage driven system, the electric field can determine the amount of charge, which can determine the degree of deformation and correspondingly the amount of change in C. To encourage multimode behavior in piezoelectric material, the piezoelectric material can be configured to be 'free floating', and in some examples, is made to be as free floating as possible in both a mechanical and electrical sense.

Damping factors of the acoustic system include a fluid Q and a crystal Q. For example, if a fluid is viscous, the Q is less. During operation, as particle clustering increases, damping increases, since there is more material in the acoustic wave. Xmin v. Q shows temperature drift, quick variations in damping as clustering, fallout occurs. Being able to track the drift and rapid variations in Q in real time permits a significant improvement in performance.

The LCL circuit can be implemented as an impedance matching network which can amplify either current or voltage depending on the value of the impedance being matched. One operation implementation technique is to amplify voltage. In this case, power may be transmitted through the LCL with little power loss with the use of low loss inductors (L) and capacitors (C).

The harmonic frequencies are reduced or eliminated due the arrangement of the elements used in the circuit and independent of whether or not there is voltage amplification. The circuit arrangement can be implemented as a low pass filter. Low pass filters allow signals below a certain frequency, called the corner frequency, to pass through the filter while blocking signals with frequencies above the corner frequency. A square wave input into such a network produces a sine wave output when the harmonics of the square wave are at frequencies above the filter's corner frequency.

In some example implementations, a multi-dimensional acoustic standing wave is utilized to trap biologic cells and cell debris from a bioreactor process, the reactance of the resonator changes. Control feedback signals can be obtained by sensing the voltage and current of the RF transmission line to the piezoelectric element. These feedback signals can be used to tune the resonator to a desired point of operation, for example to seek to optimize the acoustophoresis process. The reactance and power can be extracted from the voltage and current signals on the piezoelectric element. For example, voltage and current signals can be provided to a digital signal processor (DSP), which can be used to calculate RF reactance and power. The measured and calculated parameters of operation for the piezoelectric element can be used to provide feedback for the tuning process. This tuning process may consist of adjusting the gain of the amplifier to achieve a desired power that is provided to the piezoelectric element and/or adjusting the frequency of the drive signal to achieve a desired reactance of the resonator, as examples.

The multi-dimensional acoustic standing wave is generated through a multimode perturbation of the piezoelectric material by electronic signal generated by a function generator or oscillator and modified by an amplifier. The generation of the multi-dimensional acoustic standing wave and the multimode perturbation of the piezoelectric material is described in U.S. Pat. No. 9,228,183 which is incorporated herein by reference.

A control, which may be a digital or analog control, is provided that can receive inputs fed back from the acoustic transducer or other system components and provide control signals to various components of the acoustic system. The control can provide control signals to vary the DC output of a driver, and/or modify and control the amplitude of the power of the drive signal for the acoustic transducer. Control signals provided by the control can vary the operation of the driver to modify and control the frequency of the drive signal. The RF power driver with the control permits control and modulation of the acoustic transducer as a highly reactive load, while maintaining desired transducer and acoustic chamber performance.

The DC-DC converter may be a buck, buck-boost or boost converter, as examples, although any type of DC-DC converter may be used. The DC-DC converter may be coupled to and supply an inverter with a filter. The filter can be implemented as an LC or LCL filter with a bandwidth that permits the filter output, such as output voltage, to respond to dynamic changes of the transducer and/or the acoustic cavity.

A control technique provides a system and method for locating desired operating points for an acoustic transducer-cavity combination, with or without loading, which loading may be highly reactive. Feedback from the acoustic transducer can be used to locate the resonance and anti-resonance frequencies of transducer operation. According to some implementations, an operating frequency less than the transducer anti-resonance is inspected for minimum reactance as a point of operation. Some implementations locate a frequency above the anti-resonance frequency, which frequency is inspected for maximum reactance as a point of operation. According to these implementations, a desired level of efficiency can be obtained for acoustophoresis at designated points of operation. The points of operation that are determined according to a control technique discussed herein can be frequency setpoints, which can be dynamically maintained. For example, a desired point of operation may change as the operation or characteristics of the acoustic chamber vary. Such characteristics may include a degree of material deflection and/or separation, temperature, power delivered to the transducer, and other phenomena that may influence or modify a desired operating point.

BRIEF DESCRIPTION OF THE SEVERAL VIEWS OF THE DRAWINGS

The disclosure is described in greater detail below, with reference to the accompanying drawings, in which:

FIG. 8A is a diagram illustrating different vibrational modes for an acoustic transducer;

FIG. 8B is an isometric view of an acoustic chamber;

FIG. 8C is a left side elevation view of the acoustic chamber in FIG. 8B;

FIG. 8D is a front elevation view of the acoustic chamber in FIG. 8B;

DETAILED DESCRIPTION

Figure 1:
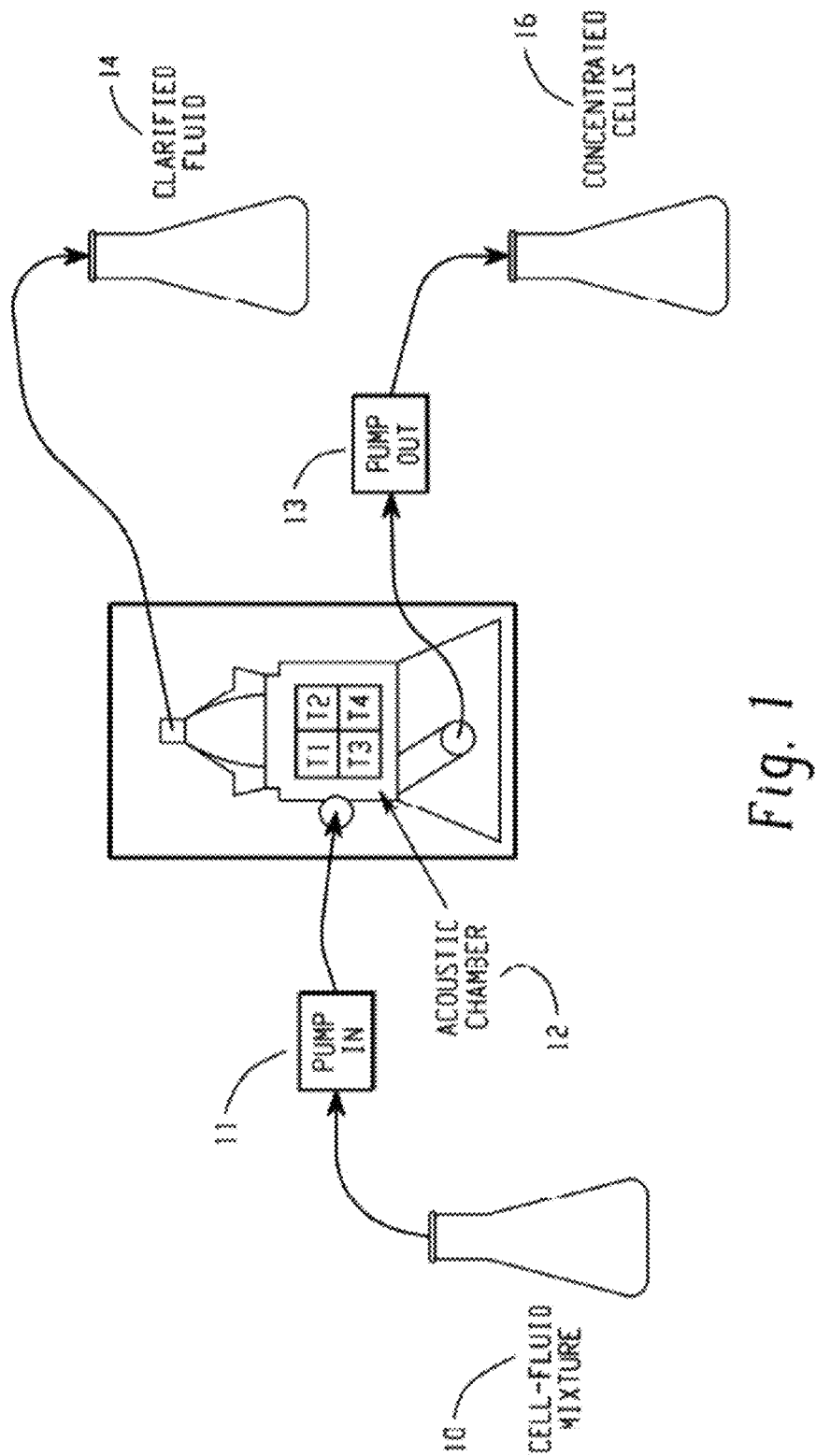
FIG. 1 is a diagram showing an acoustic chamber and connections thereto for cell clarification.

FIG. 1 is a broad overview of an acoustic wave separator system. A mixture 10 of a host fluid and a secondary phase (e.g. particles, cells, or a second different fluid) is sent via a pump 11 into an acoustic chamber 12. Here, the mixture is a cell-fluid mixture. In the acoustic chamber, the secondary phase is concentrated out of the host fluid. The concentrated cells 16 are sent by another pump 13 to be collected. The host fluid, which is more clarified due to the removal of the concentrated cells, is separately collected (indicated by reference numeral 14). Generally speaking, the acoustic chamber has at least one inlet and at least one outlet.

Figure 2:
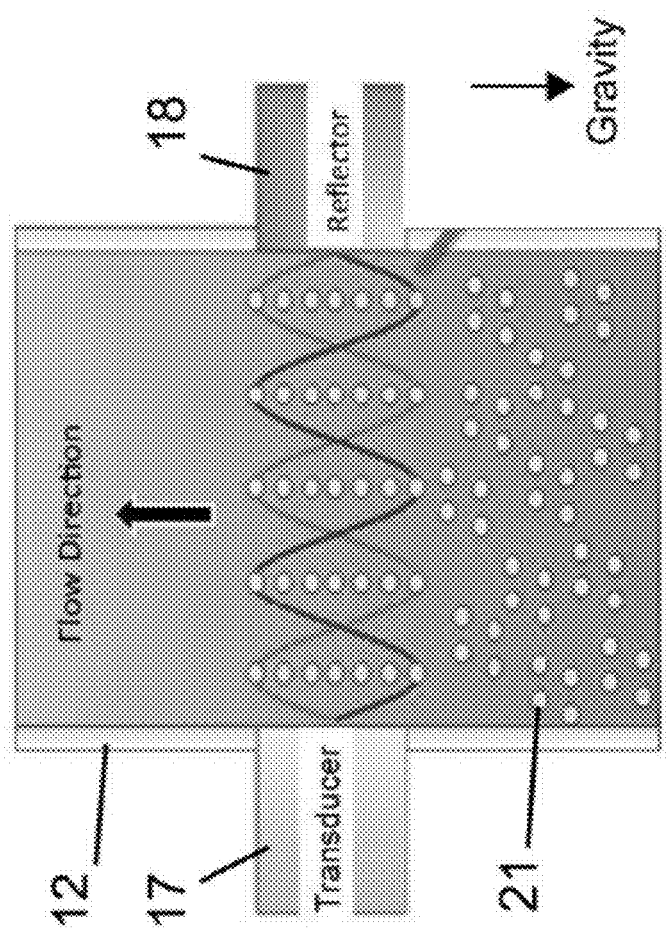
FIG. 2 is a diagram illustrating acoustophoresis with an acoustic transducer and reflector.

The acoustic chamber operates as shown in FIG. 2. One or more multi-dimensional acoustic standing waves are created between an ultrasonic transducer 17 and a reflector 18. The standing wave is illustrated as beginning and ending with local minima, however, other implementations are possible. For example, the standing wave can be offset at the transducer or the reflector so that local minima or maxima are spaced from the transducer or from the reflector. The reflected wave (or wave generated by an opposing transducer) can be in or out of phase with the transducer generated wave. The characteristics of the standing wave can be modified and/or controlled by the drive signal applied to the transducer, such as by modifying and/or controlling the phase, amplitude or frequency of the drive signal. Acoustically transparent or responsive materials may also be used with the transducer or reflector to modify and/or control the standing wave.

As the fluid mixture flows through acoustic chamber 12 with ultrasonic transducer 17 active, particles or secondary fluid 21 cluster, collect, agglomerate, aggregate, clump, or coalesce at the nodes or anti-nodes of the multi-dimensional acoustic standing wave, depending on the particles' or secondary fluid's acoustic contrast factor relative to the host fluid. The particles form clusters that eventually exit the multi-dimensional acoustic standing wave nodes or anti-nodes when the clusters have grown to a size large enough to overcome the holding force of the multi-dimensional acoustic standing wave (e.g. coalescence or agglomeration overcomes gravity or buoyancy forces). For fluids/particles that are more dense than the host fluid (such as the cells of FIG. 1), the clusters sink to the bottom and can be collected separately from the clarified host fluid. For fluids/particles that are less dense than the host fluid, the buoyant clusters float upwards and can be collected.

The scattering of the acoustic field off the particles results in a three-dimensional acoustic radiation force, which acts as a three-dimensional trapping field. The acoustic radiation force is proportional to the particle volume (e.g. the cube of the radius) when the particle is small relative to the wavelength. The force is proportional to frequency and the acoustic contrast factor. The force scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. The particle trapping in a multi-dimensional acoustic standing wave results in clustering, concentration, agglomeration and/or coalescence of the trapped particles. Relatively large solids of one material can thus be separated from smaller particles of a different material, the same material, and/or the host fluid through enhanced gravitational/buoyancy separation.

The multi-dimensional standing wave generates acoustic radiation forces in both the axial direction (e.g., in the direction of the standing wave, between the transducer and the reflector, which may be at an angle across the flow direction, and in some instances may be perpendicular to the flow direction) and the lateral direction (e.g., in the flow direction or transverse to the direction between the transducer and the reflector). As the mixture flows through the acoustic chamber, particles in suspension experience a strong axial force component in the direction of the standing wave. Since this acoustic force is across (e.g. perpendicular to) the flow direction and the drag force, it quickly moves the particles to pressure nodal planes or anti-nodal planes, depending on the contrast factor of the particle. The lateral acoustic radiation force acts to move the concentrated particles towards the center of each planar node, resulting in clustering, agglomeration or clumping. The lateral acoustic radiation force component can overcome fluid drag for such clumps of particles, to continually grow the clusters, which can exit the mixture due to gravity or buoyancy. The drop in drag per particle as the particle cluster increases in size, as well as the drop in acoustic radiation force per particle as the particle cluster grows in size, may separately or collectively influence operation of the acoustic separator device. In the present disclosure, the lateral force component and the axial force component of the multi-dimensional acoustic standing wave are of the same or different order of magnitude. In this regard, it is noted that in a multi-dimensional acoustic standing wave generated by a single transducer, the axial force is stronger than the lateral force, but the lateral force of such a multi-dimensional acoustic standing wave is much higher than the lateral force of a planar standing wave, usually by two orders of magnitude or more.

Particle drag and acoustic radiation force effects may influence optimal operation of the systems and methods of the present disclosure. At low Reynolds numbers of less than 10, laminar flow dominates, and viscous forces are much stronger than inertial forces.

As the particles are trapped by the multi-dimensional ultrasonic acoustic standing wave, they begin to aggregate and form a clump of particles. The drag on this clump of particles is a function of the geometry of the clump and is not merely the sum of the drag of the individual particles that make up the clump.

For laminar flow, the Navier Stokes equation is expressed as:

$$\rho\left(\frac{\partial V}{\partial t} + (V \cdot \nabla)V\right) = -\nabla P + \mu \nabla^2 V$$

where $$\frac{\partial V}{\partial t}$$

represents unsteady motion, $(V \cdot \nabla)V$ represents inertial motion, $-\nabla P$ represents pressure motion, and $\mu \nabla^2 V$ represents viscous motion.

For low Reynolds numbers, the unsteady motion and inertial motion terms can be ignored (i.e. set equal to zero), and the equation can be simplified to:

$$\nabla P = \mu \nabla^2 V$$

For a particle of diameter a, the following equations hold:

$$\nabla P \propto \mu \frac{V}{a}$$

$$F = 6\pi \mu a V$$

where P is pressure, $\mu$ is the dynamic viscosity, a is the particle diameter, V is the flow velocity, and F is the Stoke's drag.

Prior to discussing further optimization of the systems, it is helpful to provide an explanation now of how multi-dimensional acoustic standing waves are generated. The multi-dimensional acoustic standing wave used for particle collection is obtained by driving an ultrasonic transducer composed of a piezoelectric material at a frequency that generates the acoustic standing wave and excites a fundamental 3D vibration mode of the transducer. The transducer may be composed of various materials that may be perturbed to generate an ultrasonic wave. For example, the transducer may be composed of a piezoelectric material, including a piezoelectric crystal or poly-crystal. Perturbation of the piezoelectric material, which may be a piezoelectric crystal or poly-crystal, in the ultrasonic transducer to achieve a multimode response allows for generation of a multi-dimensional acoustic standing wave. A piezoelectric material can be specifically designed to deform in a multimode response at designed frequencies, allowing for generation of a multi-dimensional acoustic standing wave. The multi-dimensional acoustic standing wave may be generated with distinct modes of the piezoelectric material such as a 3×3 mode that generates multi-dimensional acoustic standing waves. A multitude of multi-dimensional acoustic standing waves may also be generated by allowing the piezoelectric material to vibrate through many different mode shapes. Thus, the material can be selectively excited to operate in multiple modes such as a 0×0 mode (i.e. a piston mode), 1×1, 2×2, 1×3, 3×1, 3×3, and other higher order modes. The material can be operated to cycle through various modes, in a sequence or skipping past one or more modes, and not necessarily in a same order with each cycle. This switching or dithering of the material between modes allows for various multi-dimensional wave shapes, along with a single piston mode shape to be generated over a designated time.

Some further explanation of the ultrasonic transducers used in the devices, systems, and methods of the present disclosure may be helpful as well. In this regard, the transducers may be composed of a piezoelectric material, such as a piezoelectric crystal or poly-crystal, which may be made of PZT-8 (lead zirconate titanate). Such crystals may have a major dimension on the order of 1 inch and larger. The resonance frequency of the piezoelectric material may nominally be about 2 MHz, and may be operated at one or more frequencies. Each ultrasonic transducer module can have only one crystal, or can have multiple crystals that each act as a separate ultrasonic transducer and are either controlled by one or multiple controllers, which controllers may include signal amplifiers. The piezoelectric material can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 3:
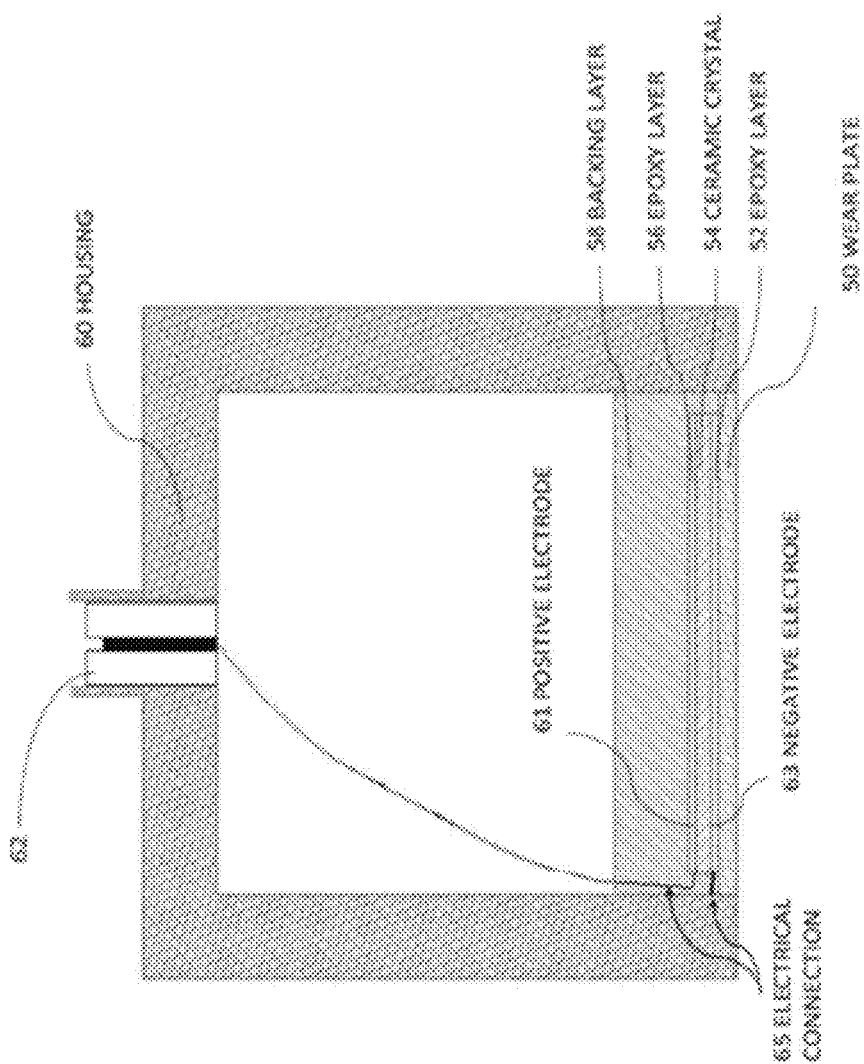
FIG. 3 is a cross-sectional side view of an acoustic transducer.

FIG. 3 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 4:
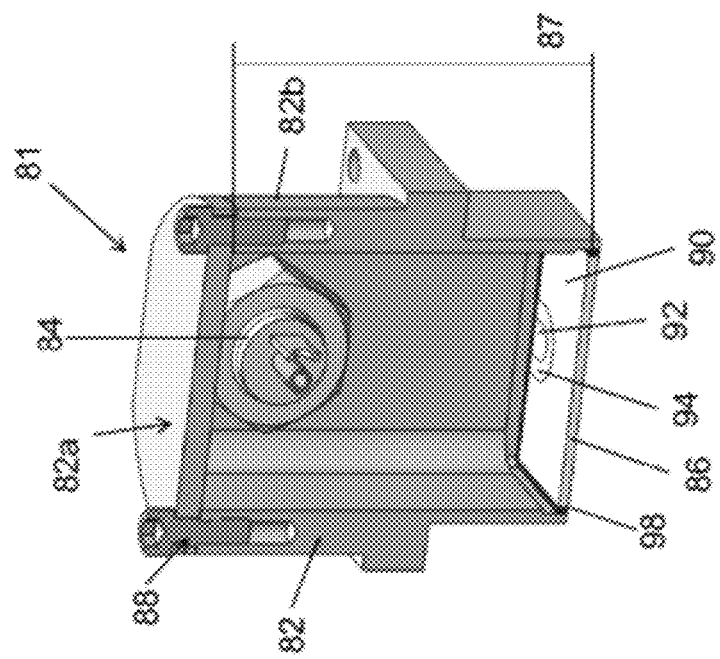
FIG. 4 is a cross-sectional side view of an acoustic transducer with a free piezoelectric element.

FIG. 4 is a cross-sectional view of an ultrasonic transducer 81 according to an example of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2-ions. As an example, a PZT (lead zirconate titanate) crystal 86 defines the bottom end of the transducer, and is exposed from the exterior of the housing. The crystal has an interior surface and an exterior surface. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 5:
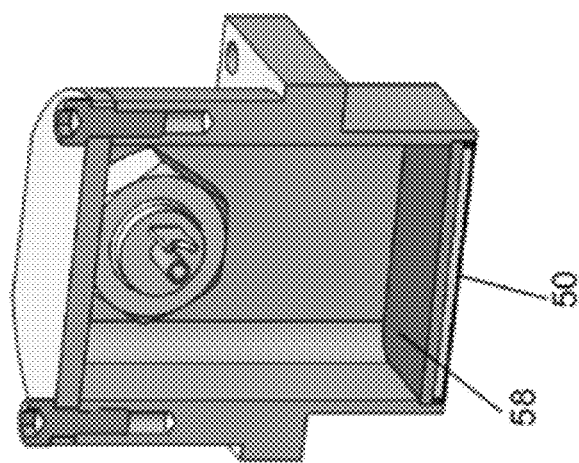
FIG. 5 is a cross-sectional view of an acoustic transducer with a damped piezoelectric element.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the housing is empty). A minimal backing 58 (on the interior surface) and/or wear plate 50 (on the exterior surface) may be provided in some embodiments, as seen in FIG. 5.

Figure 6:
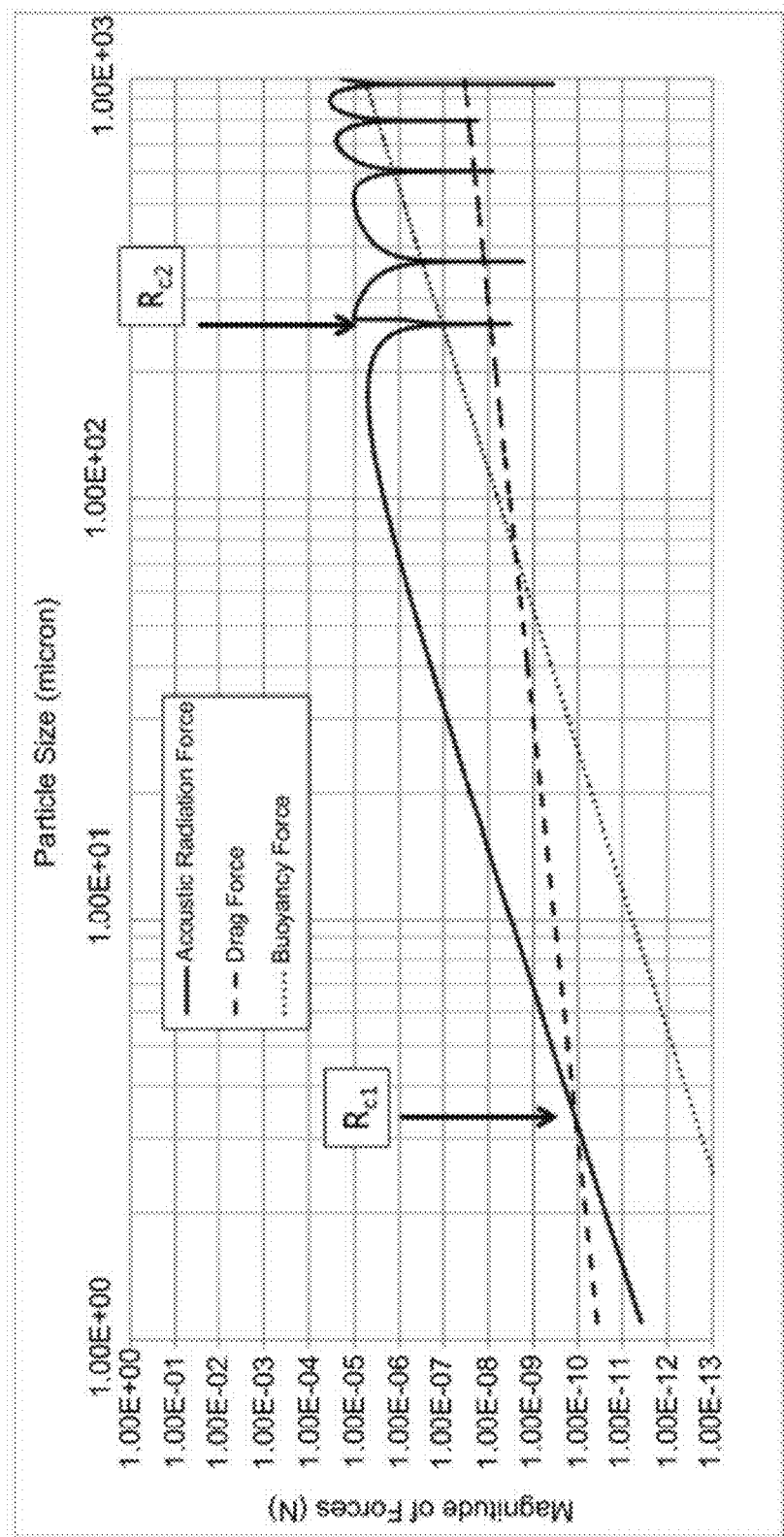
FIG. 6 is a graph illustrating force applied to a particle in a fluid.

FIG. 6 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, the acoustic radiation force balances the combined effect of fluid drag force and buoyancy force to permit a particle to be trapped in the standing wave. In FIG. 6 this trapping happens at a particle size labeled as $R_{c1}$. The graph then indicates that all larger particles will be trapped as well. Therefore, when small particles are trapped in the standing wave, particle clustering/coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles may be larger than the drag forces for the clusters to remain stationary and grow in size.

Particle size growth continues until the buoyancy force becomes dominant, which is indicated by a second critical particle size, $R_{c2}$. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size $R_{c2}$, the particles will rise or sink, depending on their relative density with respect to the host fluid. At this size, acoustic forces are secondary, gravity/buoyancy forces become dominant, and the particles naturally drop out or rise out of the host fluid. Some particles may remain in the acoustic wave as clusters of others drop out, and those remaining particles and new particles entering the acoustic chamber with the flow of a fluid mixture continue to move to the three-dimensional nodal locations, repeating the growth and drop-out process. Thus, FIG. 6 explains how small particles can be trapped continuously in a standing wave, grow into larger particles or clumps, and then eventually will rise or settle out because of increased buoyancy/gravity force.

In some examples, the size, shape, and thickness of the transducer can determine the transducer displacement at different frequencies of excitation. Transducer displacement with different frequencies may affect particle separation efficiency. Higher order modal displacements can generate three-dimensional acoustic standing waves with strong gradients in the acoustic field in all directions, thereby creating strong acoustic radiation forces in all directions, which forces may, for example be equal in magnitude, leading to multiple trapping lines, where the number of trapping lines correlate with the particular mode shape of the transducer.

Figure 7:
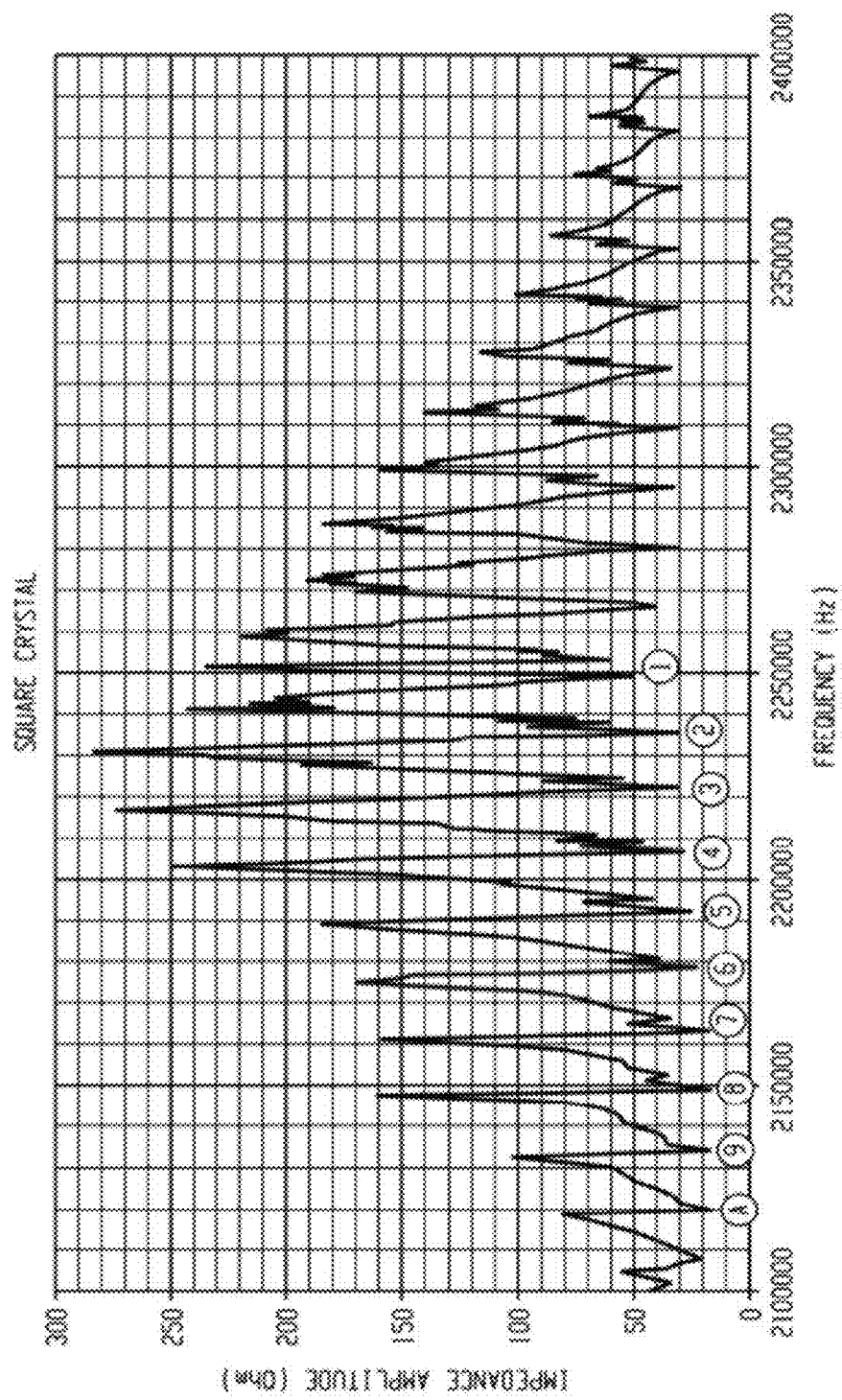
FIG. 7 is a graph illustrating impedance of a piezoelectric element.

FIG. 7 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes may not be uniform and varies depending on frequency of excitation. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 7, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 8A, for seven of the ten resonance frequencies identified in FIG. 7.

FIG. 8B shows an isometric view of the system in which the trapping line locations are being determined. FIG. 8C is a view of the system as it appears when looking down the inlet, along arrow 114. FIG. 8D is a view of the system as it appears when looking directly at the transducer face, along arrow 116.

Figure 9:
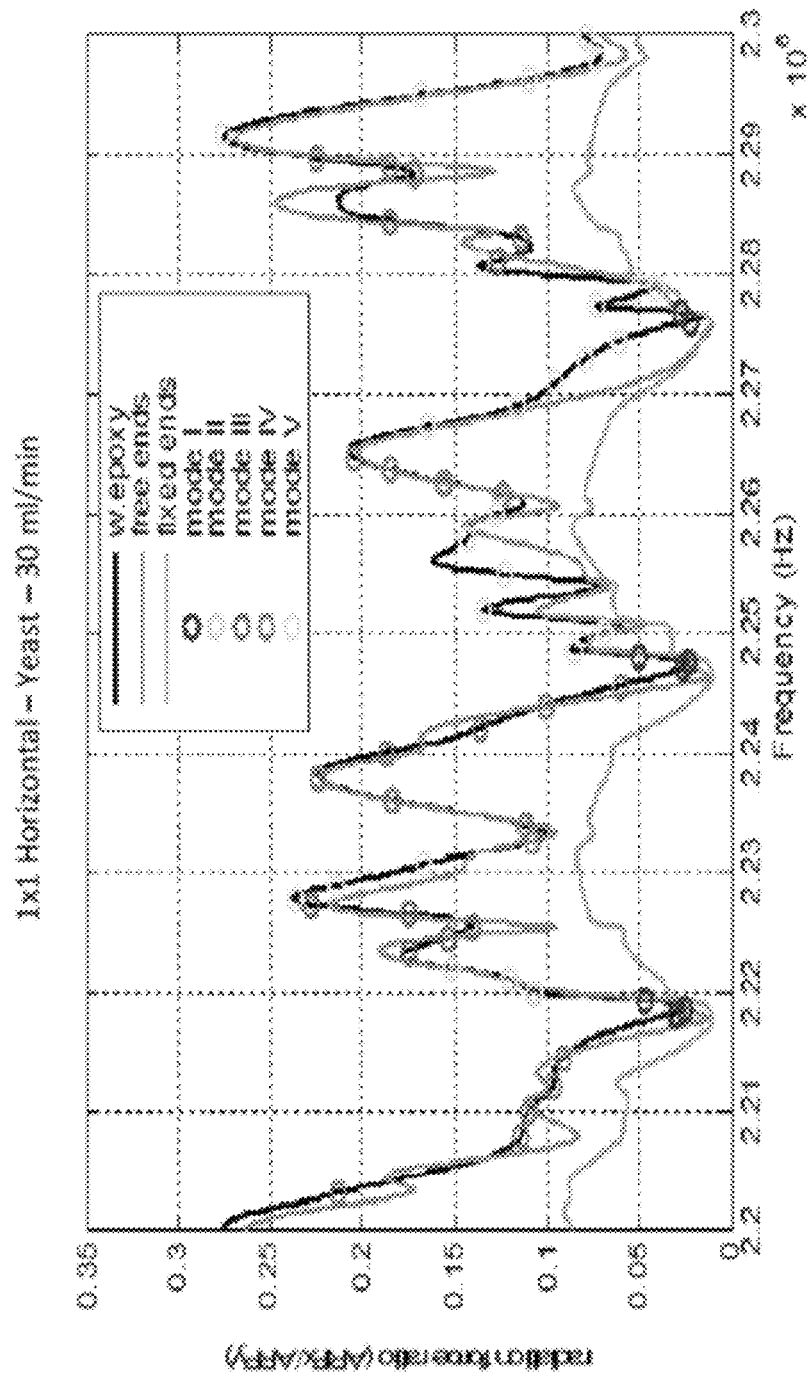
FIG. 9 is a graph illustrating transducer frequency responses and frequencies with dominant modes.

The piezoelectric crystals of the transducers described herein can be operated at various modes of response by changing the drive parameters, including frequency, for exciting the crystal. Each operation point has a theoretically infinite number of vibration modes superimposed, where one or more modes are dominant. In practice, multiple vibration modes are present at arbitrary operating points of the transducer, with some modes dominating at a given operating point. FIG. 9 presents COMSOL results for crystal vibration and lateral radiation forces on a typical particle size. The ratio of lateral to axial radiation force is plotted versus operating frequency. Points are labeled on the curve where a specific mode of vibration is dominant. Mode I represents the planar vibration mode of the crystal designed to generate a 2 MHz standing wave in a mixture. Mode III represents the 3×3 mode operation of a 1×1 crystal. These analytical results show that the 3×3 mode can be dominant with different levels of lateral radiation force. More specifically, operating the example system at a frequency of 2.283 MHz generates the lowest lateral force ratio of about 1.11 for a 3×3 mode. This operating point generates the largest cluster size and the best collection operation for the example system. Operating the devices and systems described herein at a frequency for a given configuration that produces a desired 3D mode with the lowest lateral force ratio is desirable to achieve the most efficient separation. In some embodiments, the operating point is any point on the curve that is not planar or zero phase angle. For example, an operating point can be selected on the curve in FIG. 9 where the acoustic standing wave is non-planar, and/or where the phase angle is non-zero.

Figure 10:
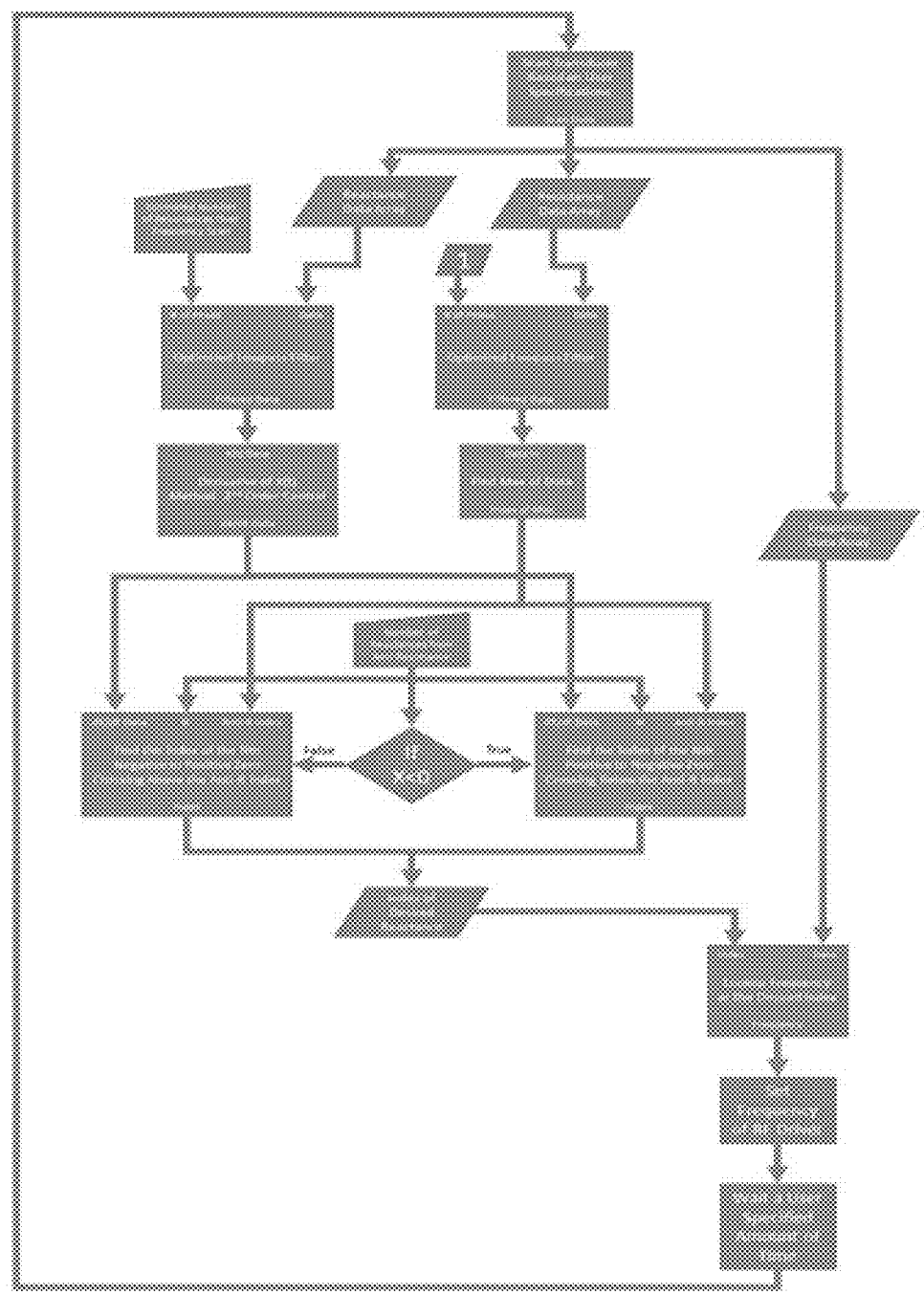
FIG. 10 is a flowchart illustrating a method for controlling an acoustic transducer.

Referring to FIG. 10, a flow chart is illustrated for a process for locating a minimum and/or maximum reactance for the acoustic transducer and/or the transducer/acoustic chamber combination, which may be under load. The load can be a fluid in the acoustic chamber, and/or particulates or a secondary fluid that is separated from the primary or host fluid. As the particulates or secondary fluid is separated from the primary or host fluid, the characteristics of the fluid in the acoustic chamber change, which can impact the operation of the transducer and/or transducer/acoustic chamber combination. The process for locating an operating point for driving the transducer begins by scanning through frequencies applied to the transducer, for example, by applying a range of frequencies to the transducer and measuring feedback data from the transducer. The range of frequencies to be scanned can be provided by user settings. Data for the reactance, X, and resistance, R, of the transducer is collected. One technique for collecting reactance and resistance data is to measure voltage, current and phase angle on the transducer. Resistance is determined as the real part of the voltage divided by the current, while reactance is determined as imaginary part of the voltage divided by the current.

As the data for the frequency scan is collected, a number of resonance and anti-resonance frequencies can be determined. The data can be passed through a low pass filter and peaks can be identified using a derivative function. A maximum peak for the anti-resonance is also identified. The method can accept an input setting of the number of reactances from anti-resonance to locate a minimum reactance. Based on the collected and calculated data, the desired minimum reactance below anti-resonance or desired maximum reactance above anti-resonance is determined, in this case as an index of the minimum or maximum reactances. Once the frequency of the desired reactance is located, the frequency of the RF power converter is set to the located frequency. The located frequency can be an operating setpoint for operating the transducer.

After a period of time, such as a number of milliseconds up to a number of tens of seconds, the process is repeated. By repeating the process, variations in the system can be dynamically identified, such as changes to reactance caused by temperature shifts, and the desired operating setpoints can be modified accordingly in keeping with the process.

Figure 11:
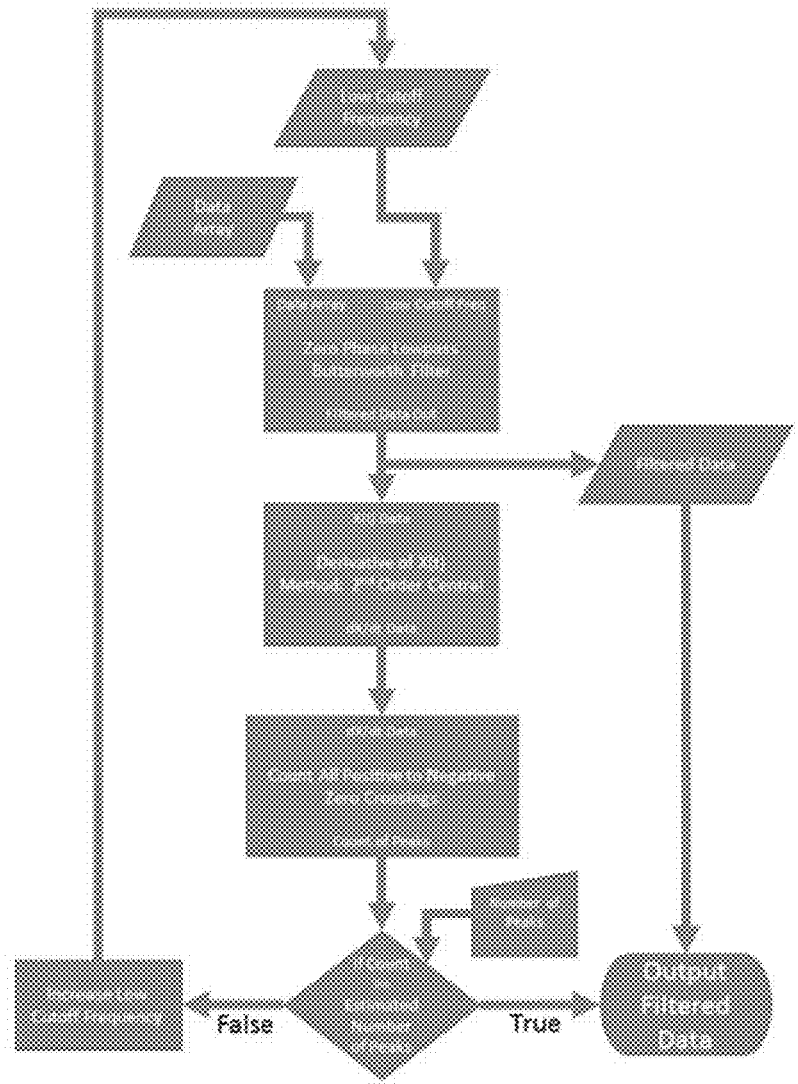
FIG. 11 is a flowchart illustrating a method for implementing an optimized low pass filter.

Referring to FIG. 11, a flow chart illustrates a process for implementing a low-pass filter for use in the frequency determination process described above. The filter characteristics can be modified in accordance with the illustrated process to contribute to optimizing detection of the desired frequency setpoints. The process begins by using an existing cut off or corner frequency in conjunction with the data collected from the frequency scan. A zero phase low-pass Butterworth filter is used to filter the collected data with the cutoff frequency. The derivative of the data is taken to determine minimums and/or maximums, and positive to negative zero crossings are identified and counted. The positive to negative zero crossings are indicative of detected peaks in the frequency response. If the process detects more peaks than expected, the cutoff frequency is increased and the process is repeated. If the count is less than the expected number of peaks, the filtered data is provided to the minimum/maximum reactance detection process.

Figure 12:
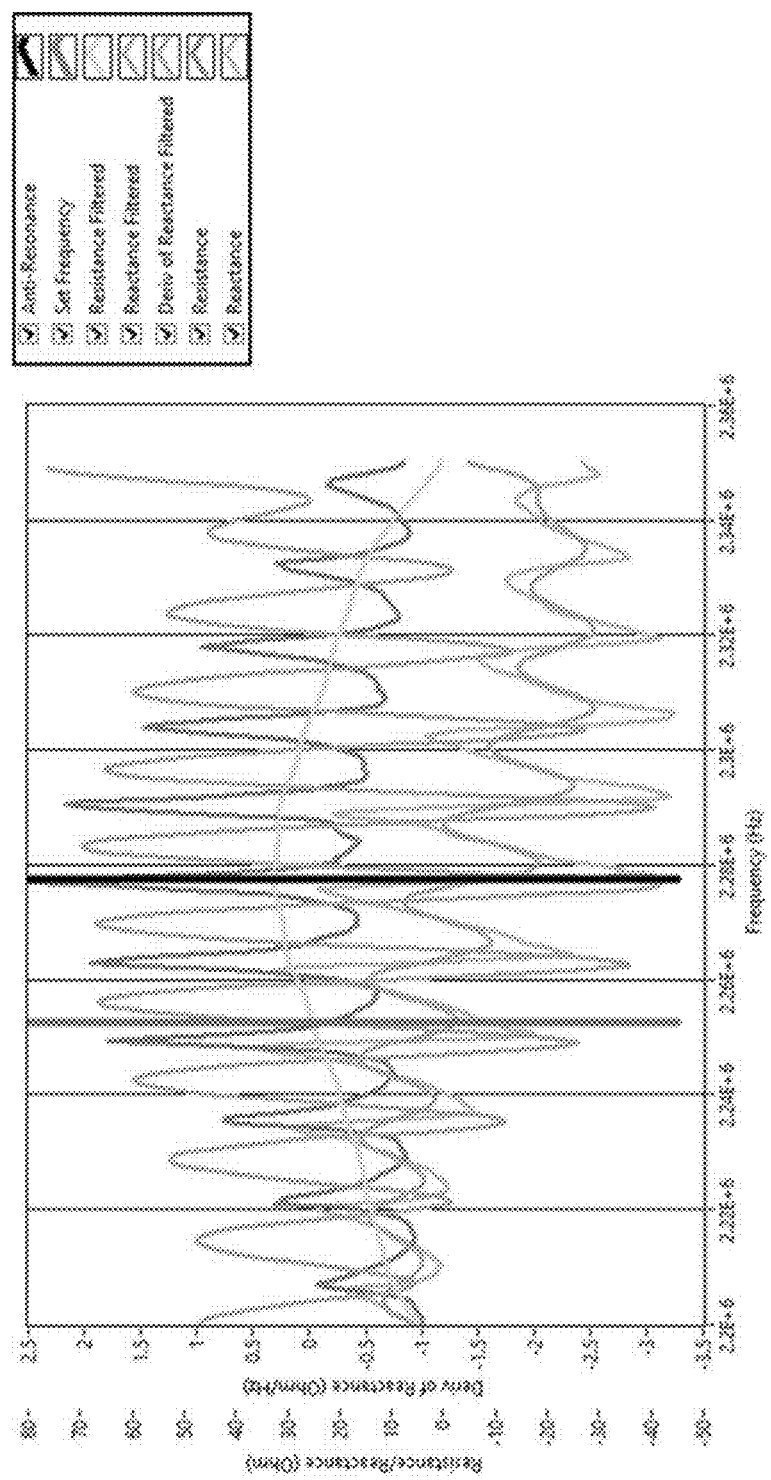
FIG. 12 is a graph illustrating a frequency response for an acoustic transducer.

FIG. 12 illustrates a frequency scan for a slightly damped 1×3 piezoelectric transducer coupled to an acoustic cavity through which a fluid containing CHO (Chinese hamster ovary) cells was flowed. As illustrated, peak anti-resonance is located, and a minimum reactance two away from the anti-resonance is selected for a frequency setpoint. In the figure, anti-resonance is approximately 2.278 MHz, and the selected frequency setpoint is approximately 2.251 MHz.

Figure 13:
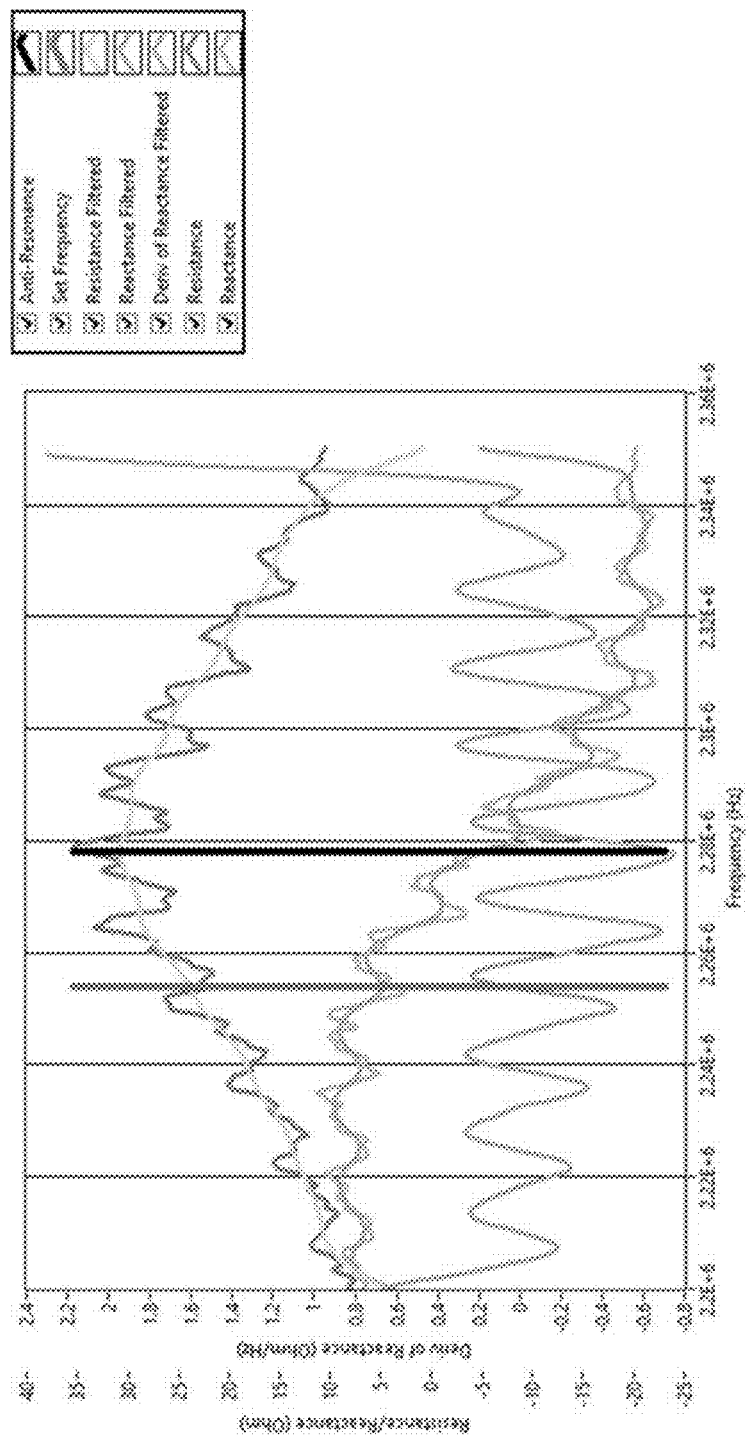
FIG. 13 is a graph illustrating a frequency response for an acoustic transducer.

FIG. 13 illustrates a frequency scan for a highly damped 2 MHz 1×3 transducer coupled to an acoustic chamber containing CHO. The peak anti-resonance is identified and the minimum reactance two away from the anti-resonance frequency is selected for an operating setpoint. Although a minimum reactance two away from the anti-resonance frequency is chosen as an operating setpoint, any reactance or index away from anti-resonance can be chosen for an operating setpoint.

Through experimental testing of the large scale acoustic filtration system, it has been determined that the 1 MHz and 2 MHz 1×3 transducer may have an optimal efficiency when operating at the minimum reactance points at frequencies below the transducer anti-resonances, as well as operating at the maximum reactance points above the anti-resonance of the transducer. The technique described herein provides an automated method to set the frequency of the RF drive to the transducer, so it is operating at a minimum reactance point below the anti-resonance or a maximum reactance above the anti-resonance. According to a feature, the technique maintains the desired operating point. The technique can be used to set the frequency of the RF drive, such as the inverter, function generator or oscillator discussed above.

The method begins by running a sweep of frequencies and collecting resistance and reactance data for each frequency step. The resistance and reactance data is extrapolated from the voltage and current measurements of the RF drive. The sweep range can be specified by the user, but is targeted to be 50 kHz above and/or 50 kHz below the anti-resonance of the transducer. In addition, or alternatively, the sweep range can be 150 kHz above and/or 150 kHz below the anti-resonance of the transducer. The step size and step interval are also variables that can be altered. When the sweep is complete it outputs the frequency, resistance, and reactance at each step.

The data from the sweep is then filtered utilizing a zero-phase low pass Butterworth filter. The reactance enters a loop where the low cutoff frequency of the filter is constantly increased, until the number of peaks of the filtered data, equals the number of estimated peaks. This number of estimated peaks is entered by the user. The resistance data is filtered using a zero-phase low-pass Butterworth filter, however the low cutoff frequency is increased until there is one peak. The peak value of the filtered resistance data is interpreted as the anti-resonance of the transducer.

The derivative of the filtered reactance data is calculated and is used to find all the maximum or minimum points of the reactance curve. If the number of reactance minima/maxima from the anti-resonance data input is negative the method will look for the minimum reactance points below the anti-resonance. The method does this by identifying the negative to positive zero crossings, in other words, the upward slope zero crossings of the derivative of the filtered reactance curve. If this number is positive the method will look for the positive to negative zero crossings above the anti-resonance, which are the maximum points of the reactance curve. The absolute value of the number of reactance minima/maxima from the anti-resonance data input is the number of minimum or maximum points from the anti-resonance. The index of this point is used to determine the frequency to set the RF drive.

The RF drive is set and the method waits for a designated amount of time set by the user. Once this time period has elapsed the method then scans and start the sequence over again. Sample data of both slightly and highly damped data can be seen in FIG. 12 and in FIG. 13. In both these examples the method was selected to pick two minimum reactance points below the anti-resonance, represented by heavy vertical lines. The set frequency is indicated by the heavy line to the left. It can be seen that this line falls on the negative to positive zero crossing of the derivative of the filtered reactance data curve, and at the local minimum of the filtered reactance data curve.

Figure 14:
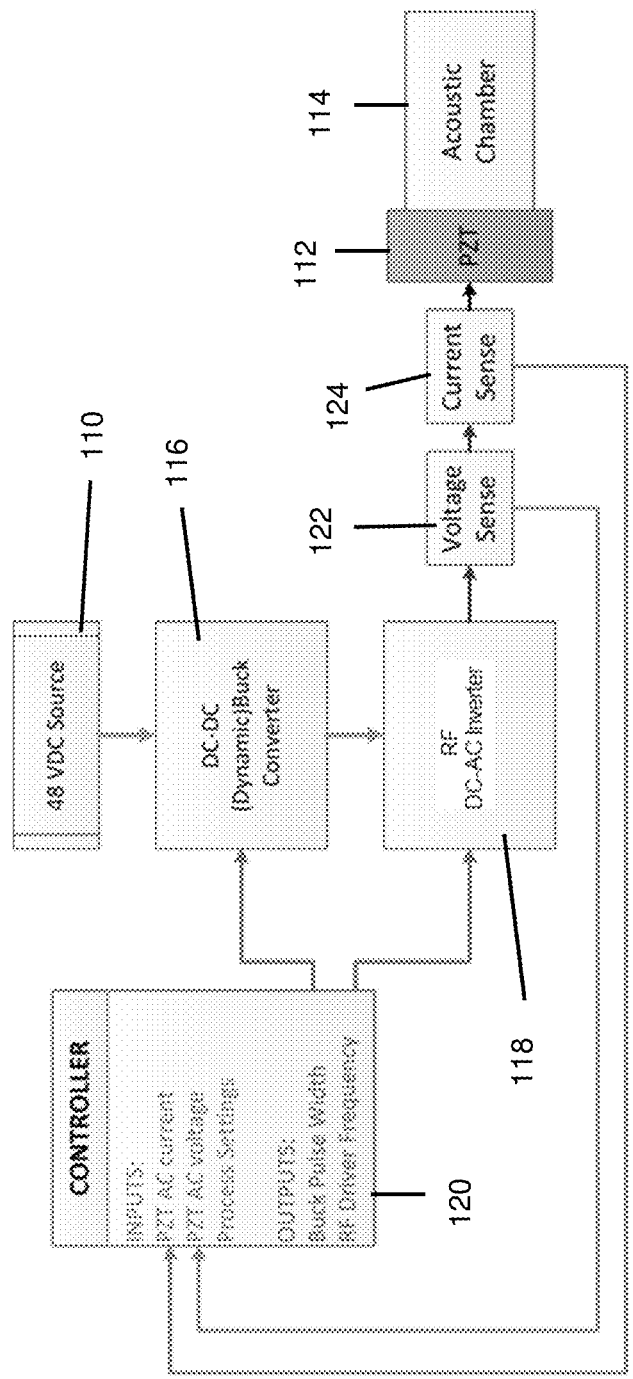
FIG. 14 is a block diagram illustrating a control technique for an acoustic transducer.

Referring to FIG. 14, a diagram of a control configuration for controlling an acoustic transducer 112 coupled to an acoustic chamber 114 is illustrated. Acoustic transducer 112 is driven by an RF power converter composed of DC source 110, DC-DC converter 116 and RF DC-AC inverter 118. The output drive signal provided by inverter 118 is inspected or sensed to obtain voltage sense 122 and current sense 124, which are fed back to a controller 120. Controller 120 provides control signals to converter 116 and inverter 118 to modulate the drive signal provided to the acoustic transducer 112.

The signal provided by controller 120 to converter 116 is a pulse width measure, which determines the duty cycle of the switching signals in converter 116. The duty cycle determines the DC level of the output of converter 116, which is applied to inverter 118. For example, the greater the duty cycle, the higher the DC output that is generated by converter 116. Controller 120 also provides control signals to inverter 118 that determine the frequency of operation of inverter 118. The control signals provided to inverter 118 may be switching signals, for switching switches in inverter 118. Alternately, or in addition, controller 120 can provide a control signal to inverter 118 that is used to indicate a desired switching frequency, and circuitry internal to inverter 118 interprets the control signal and switches the internal switches in accordance with the interpreted control signal.

Voltage sense 122 and current sense 124 produce signals that are provided to controller 120 as feedback signals to control the drive signal provided to acoustic transducer 112. Controller 120 performs operations and calculations on the signals provided by voltage sense 122 and current sense 124, for example, to obtain a power measure, $P=V*I$, where P is power such as real power, imaginary power or apparent power, and where V is voltage such as peak voltage or root mean squared (rms) voltage and I is current. As an example, real power is represented by the equation $P=V*I*\cos(\text{phase angle})$.

Controller 120 is provisioned with a control scheme that accepts process settings, such as power output, range of frequency operation, or other user selectable parameters, and provides control signals to converter 116 and inverter 118 based on the process settings and the feedback values. For example, as described above, controller 120 can sequence through a number of frequencies in a range of frequencies that are provided to inverter 118 to scan through the frequency range and determine the characteristics of transducer 112 or transducer 112 in combination with acoustic chamber 114, which may be under load. The results of the frequency scan in terms of voltage and current obtained from the voltage sense 122 and current sense 124, respectively, are used to identify characteristics of the impedance curves for the components or the system, such as is illustrated in FIG. 12. The frequency scan can be implemented to occur at set up, and/or at intervals during operation of the illustrated system. During steady-state operation, the frequency scanned can be conducted to identify desired setpoints for operation, such as power or frequency, based on user settings and feedback values. The control scheme implemented by controller 120 is thus dynamic, and responds to changing conditions in the system, such as may be encountered with frequency drift, temperature change, load changes and any other system parameter changes. The dynamic nature of the control scheme permits the controller to respond to or compensate for nonlinearities, such as may be encountered as components age or lose tolerance. Accordingly, the control scheme is adaptive and can accommodate system changes.

Some examples of system operation include driving acoustic transducer 112 to produce a multidimensional acoustic standing wave in the acoustic chamber 114. A 3D acoustic wave is stimulated by driving acoustic transducer 112, which may be implemented as a piezoelectric crystal, sometimes referred to herein as a PZT, near its anti-resonance frequency. Cavity resonances modulate the impedance profile of the PZT as well as affect its resonance modes. Under the influence of the 3D acoustic field, suspended particles in the liquid medium in the acoustic cavity 114 are forced into agglomerated sheets and then into tightly packed clusters of agglomerated material. Once particle concentrations reach a critical size, gravitational forces take over and the agglomerated material drops out of the acoustic field and to the bottom of the chamber. The changing concentrations of agglomerated material as well as the dropping out of that material affects the cavity's resonances which in turn change the acoustic loading on the PZT and its corresponding electrical impedance. The changing dynamics of the collected material detunes the cavity and PZT reducing the effects of the 3D wave in clarifying the medium. Additionally, changes in the medium and cavity temperature also detune the cavity so that clarification is reduced. To track the resonance changes occurring in the cavity, a control technique is used to follow changes in the PZT's electrical characteristics.

A strong 3D acoustic field can be generated by driving the PZT at a frequency where its input impedance is a complex (real and imaginary) quantity. However, cavity dynamics can cause that impedance value to change significantly in an erratic manner. The changes in impedance are due, at least in part, to changes in the load applied to the acoustic transducer 112 and/or acoustic chamber 114. As particles or secondary fluid is separated from a primary or host fluid, the loading on acoustic transducer 112 and/or acoustic chamber 114 changes, which in turn can influence the impedance of the acoustic transducer 112 and/or acoustic chamber 114.

To correct for detuning, controller 120 calculates the PZT impedance from the voltage and current sensed at the PZT using voltage sense 122 and current sense 124 and determines which way to change the operating frequency to compensate for the detuning. Since frequency changes affect power delivered to the chamber, the controller also determines how to adjust the output voltage of (dynamic) buck converter 116 to maintain the desired amount of power output from RF DC-AC inverter 118 and into the acoustic transducer 112 and/or acoustic chamber 114.

Buck converter 116 is an electronically adjustable DC-DC power supply and is the power source for inverter 118. RF DC-AC inverter 118 converts the DC voltage out of converter 116 back to a high-frequency, AC signal to drive the PZT. The dynamics in the chamber occur at rates corresponding to frequencies in the low audio band. Consequently, the converter 116, controller 120, and DC-AC inverter 118 are capable of working at rates faster than the low audio band to permit controller 120 to track chamber dynamics and keep the system in tune.

Controller 120 can simultaneously change the frequency of DC-AC inverter 118 and the DC voltage coming out of buck converter 116 to track cavity dynamics in real time. The control bandwidth of the system is a function of the RF bandwidth of inverter 118 and the cutoff frequency of the filtering system of buck converter 116.

Controller 120 can be implemented as a DSP (digital signal processor) control, or as an FPGA (field programmable gate array) control, as examples. Controller 120 may be implemented with two channels, to permit parallel processing, for example to analyze real and/or reactive impedance, voltage, current and power.

The acoustic dynamics of the cavity affects the electrical characteristics of the PZT which affects the voltage and current drawn the PZT. The sensed PZT voltage and current is processed by the controller to compute the real-time power consumed by the PZT as well as its instantaneous impedance (affected by acoustic dynamics). Based on user set points the controller adjusts, in real-time, the DC power supplied to inverter 118 and the frequency at which inverter 118 is operated to track cavity dynamics and maintain user set points. An LCL network is used to match the output impedance of inverter t 118 to increase power transfer efficiency.

Controller 120 samples sensor signals fast enough to detect changes in cavity performance (via changes in PZT impedance) in real time. For example, controller 120 may sample the feedback values from the voltage sense 122 and current sense 124 at one hundred million samples per second. Signal processing techniques are implemented to permit a wide dynamic range for system operation to accommodate wide variations in cavity dynamics and applications. Converter 116 can be configured to have a fast response time to follow the signal commands coming from controller 120. Inverter 118 can drive a wide range of loads that demand varying amounts of real and reactive power that change over time. The electronics package used to implement the system illustrated in FIG. 14 may be configured to meet or exceed UL and CE requirements for electromagnetic interference (EMI).

Figure 15:
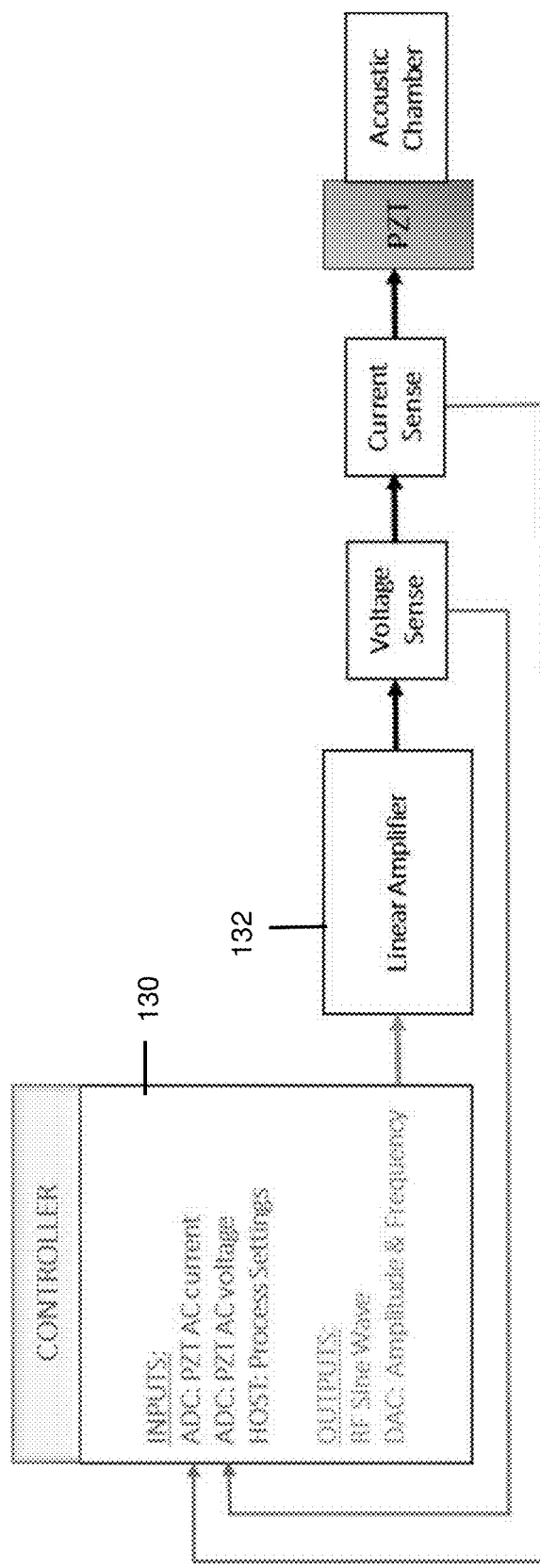
FIG. 15 is a block diagram illustrating a control technique for an acoustic transducer.

Referring to FIG. 15, controller 120 may be implemented with very-high-speed parallel digital-signal-processing loops using RTL (Register Transfer Level) which is realized in actual digital electronic circuits inside a field-programmable-gate-array (FPGA). Two high speed digital proportional integral (PI) loops adjust the frequency and amplitude control signals generated by controller 120 to track power and reactance. A linear amplifier 132 is used to amplify the output signal from controller 130 (which can be implemented as controller 120) in preparation for driving the PZT. The voltage and current sense is used to sense the voltage and current at the transducer. A calculation is performed in series by controller 130 to generate control signals provided to linear amplifier 132. The FPGA can be operated with a clocking signal of 100 MHz. The clocking speed contributes to obtaining fast enough sampling to monitor and adapt to conditions of the PZT in real-time. In addition, the structure of the FPGA permits each gate component to have a propagation delay commensurate with the clocking speed. The propagation delay for each gate component can be less than one cycle, or 10 ns with a clocking speed of 100 MHz.

Controller 130 may be configured to calculate the following parameters.

$VRMS = sqrt(V1^2 + V2^2 + \ldots + Vn^2)$
$IRMS = sqrt(I1^2 + I2^2 + \ldots + In^2)$
Real Power (P=V-Inst.×I-Inst Integrated over N Cycles)
Apparent Power (S=VRMS×IRMS)

Figure 16:
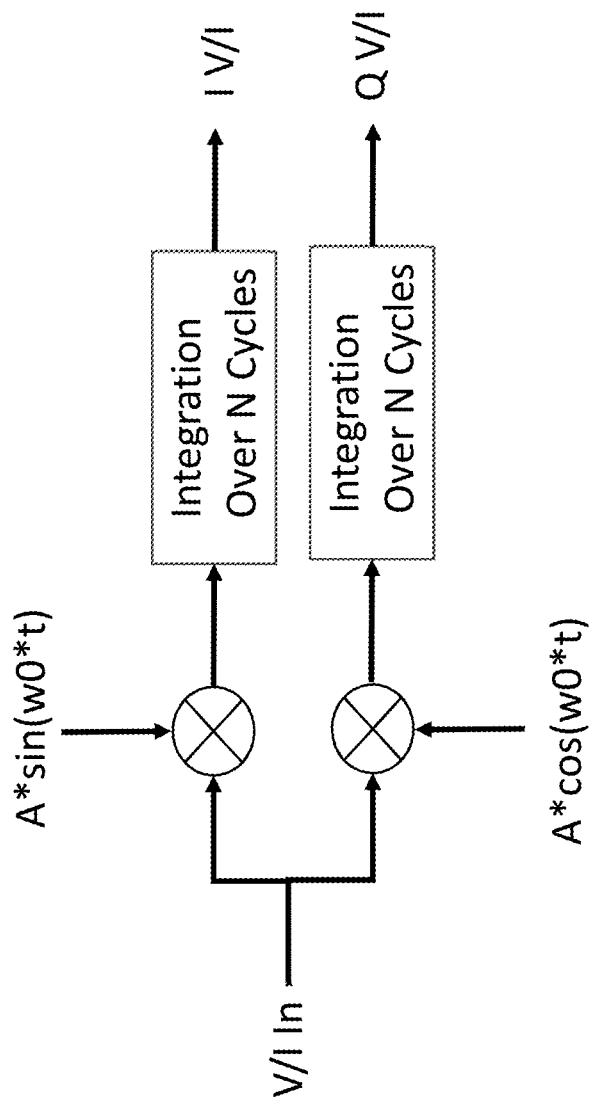
FIG. 16 is a block diagram illustrating demodulation of a voltage or current signal.

Controller 130 may be configured to calculate reactive power and bipolar phase angle by decomposing sensed voltage and current into in-phase and quadrature-phase components. FIG. 16 illustrates the in-phase and quadrature-phase demodulation of the voltage and current to obtain a four-quadrant phase, reactive power and reactance. The calculations for reactive power and phase angle can be simplified using the in-phase and quadrature-phase components.

VPhase Angle=Arctan(QV/IV)
IPhase Angle=Arctan(QI/II)
Phase Angle=VPhase−Iphase
Reactive Power=(Q=Apparent Power×Sine(Phase Angle)

Controller 130 may implement a control scheme that begins with a frequency sweep to determine system performance parameters at discrete frequencies within the frequency sweep range. The control scheme may accept inputs of a start frequency, a frequency step size and number of steps, which defines the frequency sweep range. Controller 130 provides control signals to linear amplifier 132 to modulate the frequency applied to the PZT, and the voltage and current of the PZT are measured using the voltage sense and the current sense. The control scheme of controller 130 may repeat the frequency sweep a number of times to determine the system characteristics, for example, reactance, with a relatively high level of assurance.

A number of reactance minimums can be identified as a result of analysis of the data obtained in the frequency sweep. The control technique can be provided with an input that specifies a certain frequency range where a desired reactance minimum is located, as well as being provided with a resistance slope (+/−) that can be used for tracking a desired point of operation based on resistance tracking that corresponds to a desired minimum reactance. The resistance slope may be constant near the minimum reactance, which may provide a useful parameter for use with a tracking technique. By tracking resistance at a desired frequency, a robust control can be attained for operating at a minimum reactance point.

The control technique may take the derivative of the resistance/reactance values to locate zero slope derivatives, which are indicative of maximums and minimums. A proportional-integral-differential (PID) controller loop may be used to track the resistance to obtain a frequency setpoint at which a desired minimum reactance occurs. In some implementations, the control may be a proportional-integral (PI) loop. With the FPGA operating at 100 MHz, adjustments or frequency corrections can be made every 10 ns to compensate for changes in the tracked resistance. This type of control can be very accurate and implemented in real-time to manage control of the PZT in the presence of a number of changing variables, including reactance, load and temperature, for examples. The control technique can be provided with an error limit for the frequency of the reactance minimum or frequency setpoint, to permit the control to adjust the output to linear amplifier 132 to maintain the frequency within the error limit.

A fluid mixture, such as a mixture of fluid and particulates, may be flowed through the acoustic chamber to be separated. The fluid mixture flow may be provided via a fluid pump, which may introduce perturbations to the fluid, as well as the PZT and chamber. The perturbations can create a significant fluctuation in sensed voltage and current amplitudes, indicating that the effective impedance of the chamber fluctuates with pump perturbations. However, owing to the speed of the control technique, the fluctuations can be almost completely canceled out by the control method. For example, the perturbations can be identified in the feedback data from the PZT and can be compensated for in the control output from the controller. The feedback data, for example the sensed voltage and current, may be used to track the overall acoustic chamber pressure. As the characteristics of the transducer and/or acoustic chamber change over time and with various environmental parameters, such as pressure or temperature, the changes can be sensed and the control technique can compensate for the changes to continue to operate the transducer and acoustic chamber at a desired setpoint. Thus, a desired setpoint for operation can be maintained with very high accuracy and precision, which can lead to optimized efficiency for operation of the system.

The FPGA may be implemented as a standalone module and maybe coupled with a class-D driver. Each module may be provided with a hardcoded address so that it can be identified when connected to a system. The module can be configured to be hot-swappable, so that continuous operation of the system is permitted. The module may be calibrated to a particular system and a transducer, or may be configured to perform a calibration at particular points, such as upon initialization. The module may include long-term memory, such as an EEPROM, to permit storage of time in operation, health, error logs and other information associated with operation of the module. The module is configured to accept updates, so that new control techniques can be implemented with the same equipment, for example.

An example control technique performs a loop in which voltage and current are measured at the acoustic transducer, real power and resistance are calculated and provided to a proportional-integral (PI) controller. The output of the PI controller is used to adjust the amplitude and frequency of the signal supplied to the transducer. The loop is repeated, resulting in the amplitude of the power provided to the transducer being controlled and tracked, and the frequency of the power provided to the transducer being controlled and tracked. The loop permits the controller to dynamically adjust to changes in the system, including changes related to loading of the transducer and/or the transducer/acoustic cavity combination or changes related to temperature, as examples.

Figure 17:
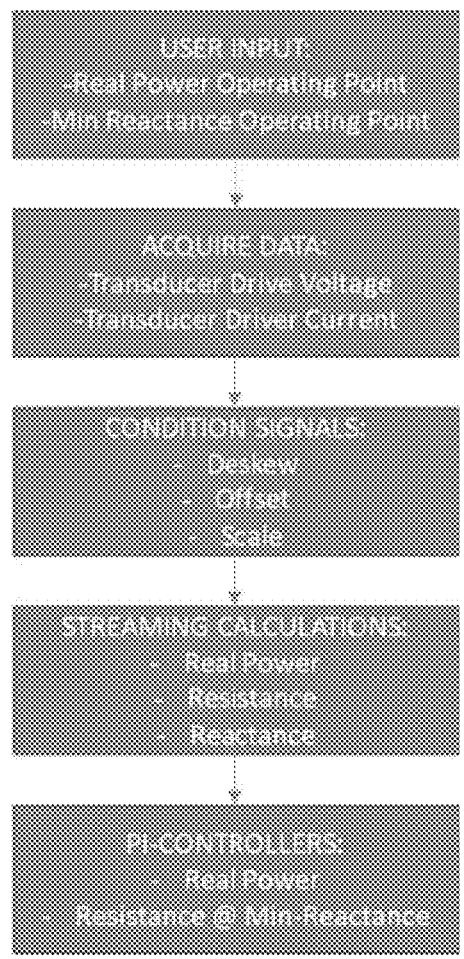
FIG. 17 is a flowchart illustrating components of a control technique for use with an acoustic transducer.

FIG. 17 illustrates an example method for processing information to implement a transducer control. The method uses desired operating points for real power and a minimum reactance, which may be obtained from user input. Data is received from the transducer, including drive voltage and drive current. The data received from the transducer is conditioned to improve the quality of the information and calculations derived there from. For example, the data representing drive voltage and drive current is deskewed (phase balance the relationship between the voltage and current signals), provided with an offset and scaled for use with subsequent calculations. The condition data is used to calculate real power, resistance and reactance of the transducer. These parameters are compared to operating points received in the method, and a PI controller is used to generate a signal that can adjust the real power and frequency of the drive signal provided to the transducer. Note that the conditioned feedback parameters can be used to generate an error signal in conjunction with the desired operating point information, with the error signal being provided to an amplifier that adjusts the signal provided to the power supply, whether linear amplifier or converter-inverter combination.

The acoustic radiation force exerted on the particles in the fluid can be calculated and/or modeled. For example, a COMSOL model was created and used to predict linear acoustic standing wave fields. The model implemented models for piezo-electricity, elasticity and acoustics. The model was used to predict acoustic radiation forces on particles that are small compared to wavelength, which includes using the Gorkov equation, and larger particles, which includes using the Yurii-Zhenia equations. In some instances, it may be helpful to normalized the results, for example, by normalizing with respect to power. The effect on the particles of the acoustic radiation forces can be studied, and in particular used for determining transducer configurations, and for controlling the transducer and/or transducer/cavity combination.

Figure 18:
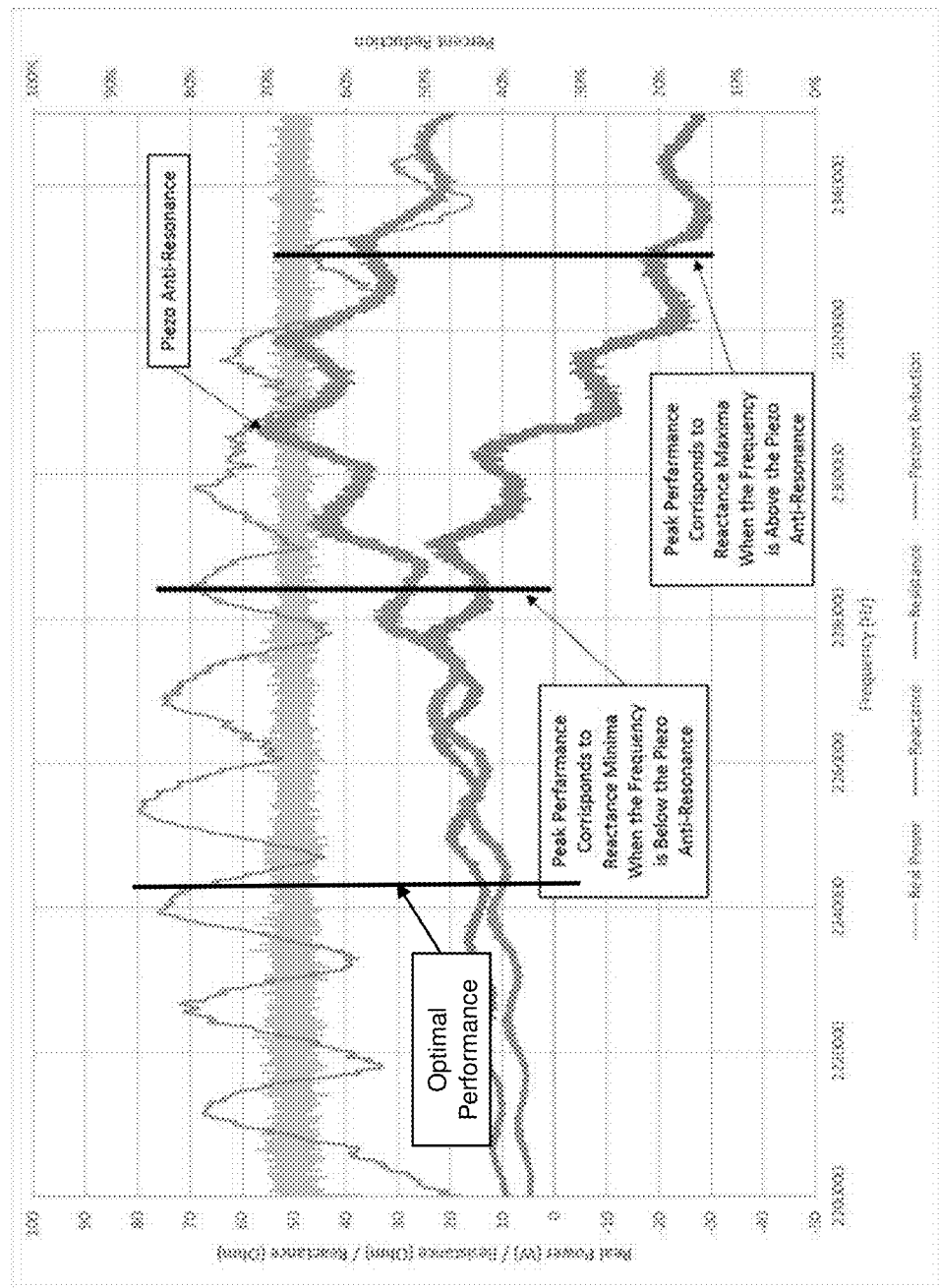
FIG. 18 is a graph illustrating power, reactance, resistance and peak performance for an acoustic transducer.

FIG. 18 is a graph illustrating impedance (resistance and reactance), power and performance of an acoustophoretic system described herein. As can be seen in the graph, peak performance occurs at reactance minimums. Optimal performance may occur where a resistance maxima and a reactance minima nearly coincide.

Figure 19:
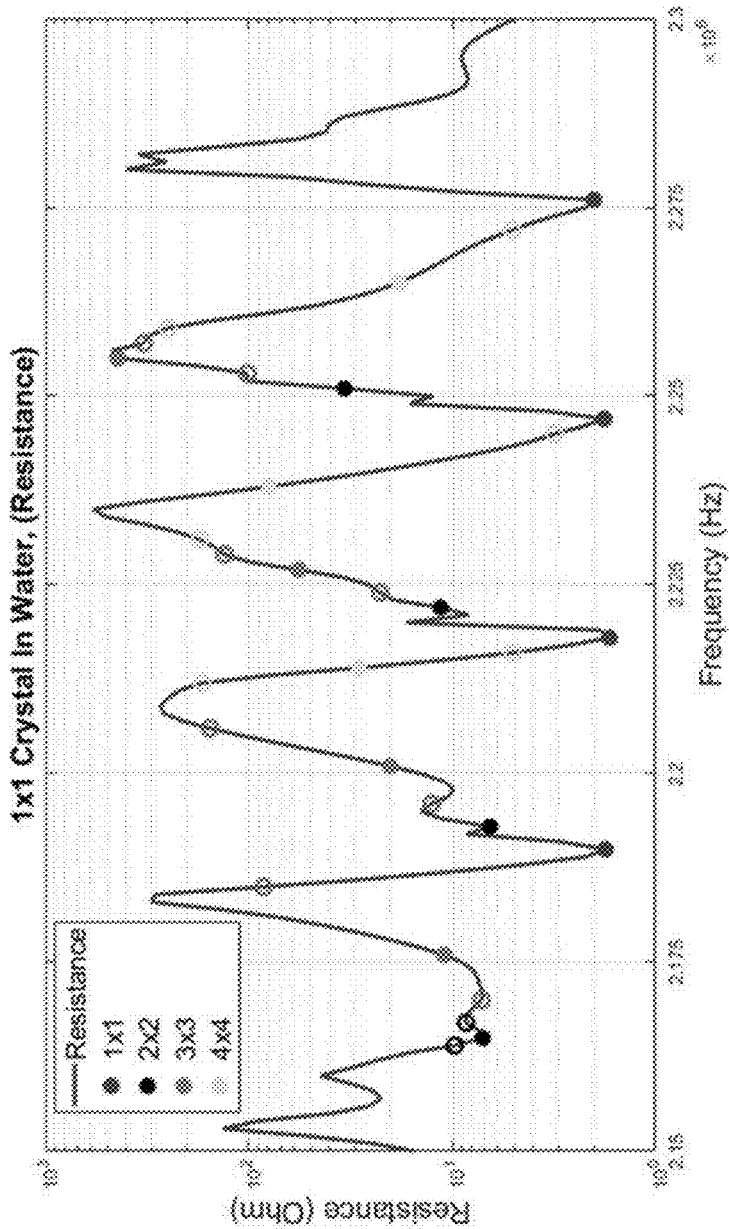
FIG. 19 is a graph illustrating a resistance curve versus frequency.
Figure 20:
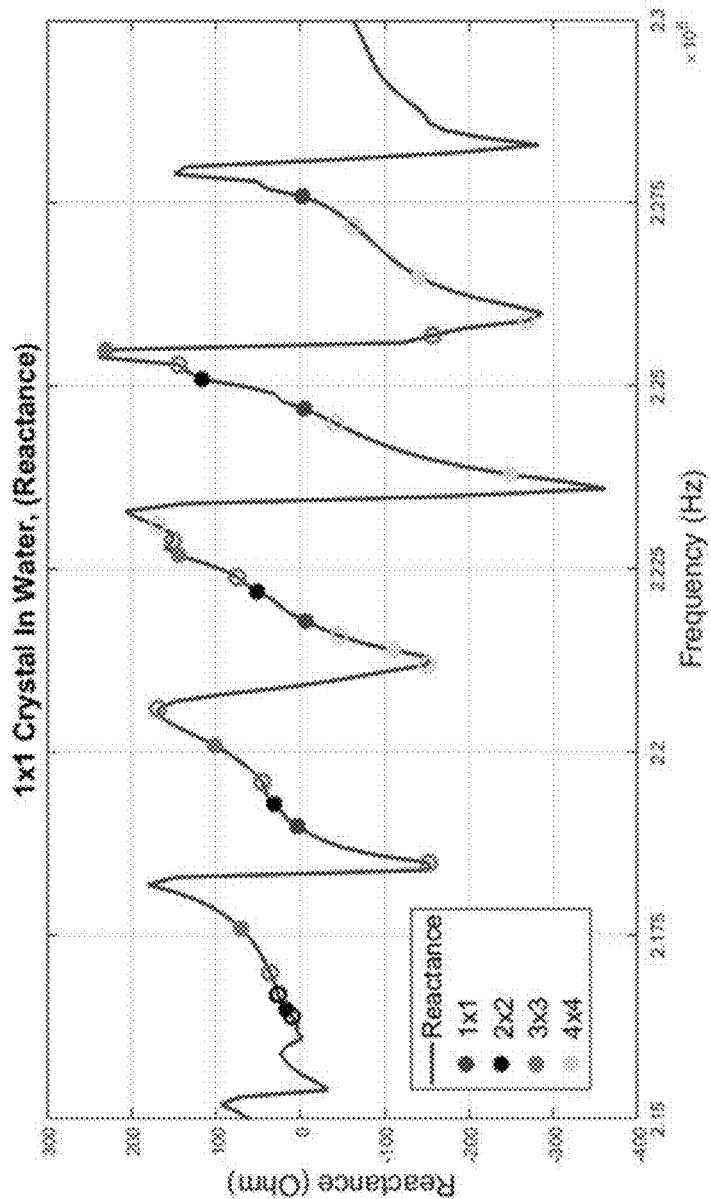
FIG. 20 is a graph illustrating reactance versus frequency, with a number of different modes identified.

FIG. 19 is a graph illustrating a resistance curve versus frequency, with a number of different modes identified. Higher order modes are obtained along the graph line locations where resistance is above a minimum. FIG. 20 is a graph illustrating reactance of an acoustic system over a range of 2.15 MHz to 2.3 MHz. The graph illustrates that the selection of the Xmin point of operation may depend on the mode. For example, the graph shows that the lowest Xmin is for a 4×4 mode, meaning that the best performance may be obtained by running the system at a frequency that excites the transducer in a 4×4 mode of operation and selecting the appropriate Xmin, e.g., x-1, x-2, whichever is strongest.

Figure 21:
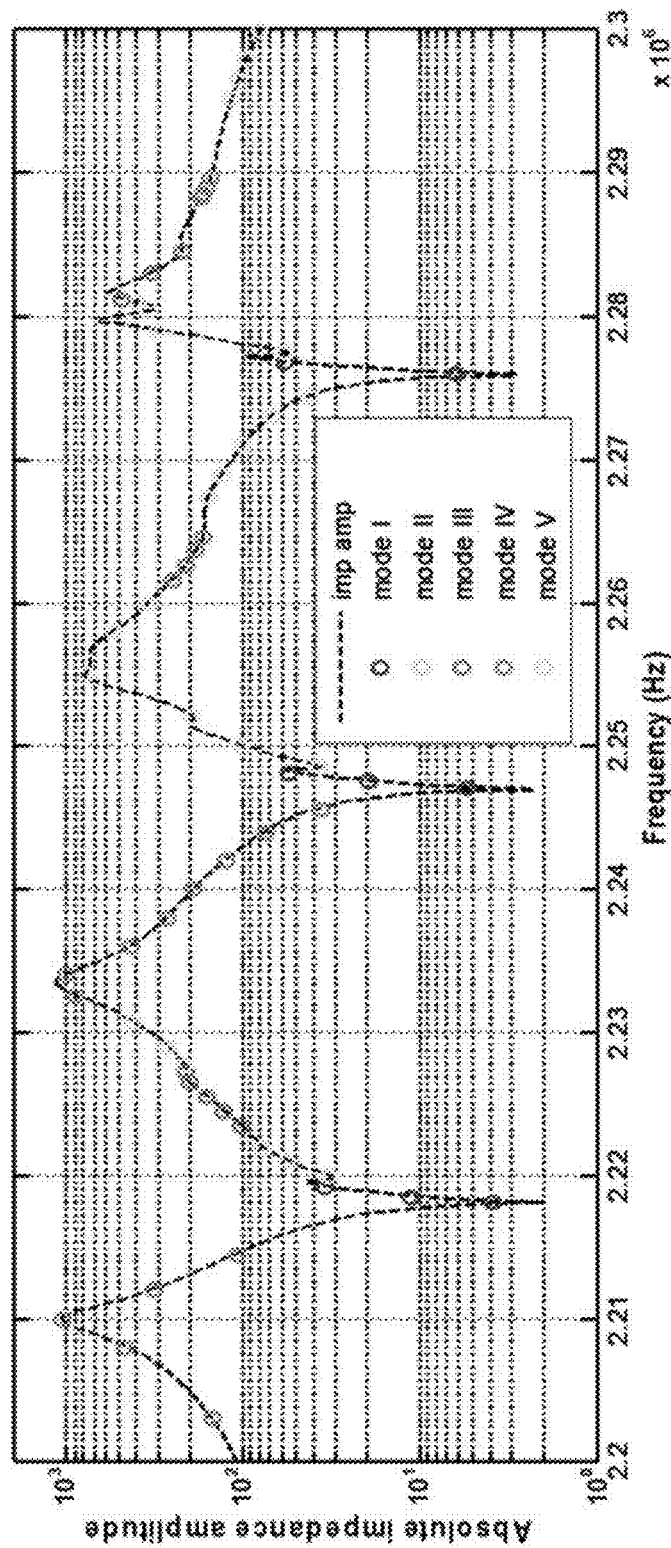
FIG. 21 is a graph illustrating absolute impedance amplitude.

FIG. 21 is a graph illustrating absolute impedance amplitude. The graph illustrates that the best multimode performance points are near a sharp slope, making it difficult to maintain high performance.

Figure 22:
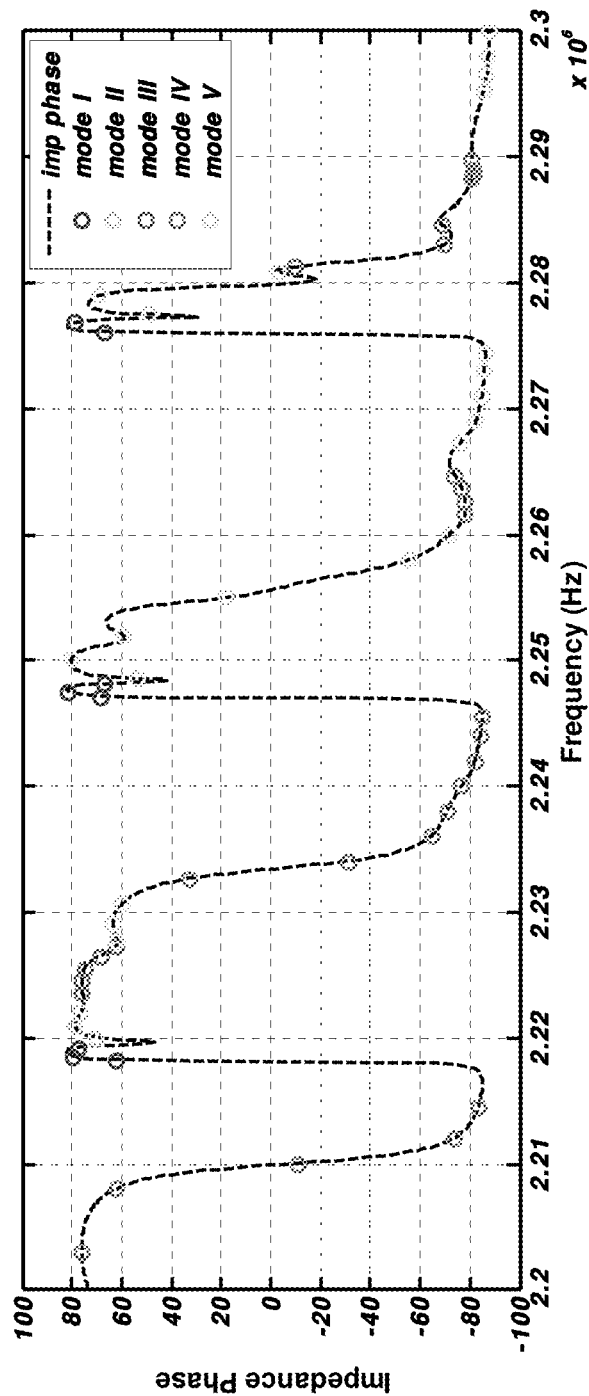
FIG. 22 is a graph illustrating impedance phase.

FIG. 22 is a graph illustrating impedance phase. The most negative phase represents the minimal reactances, or Xmin.

Figure 23:
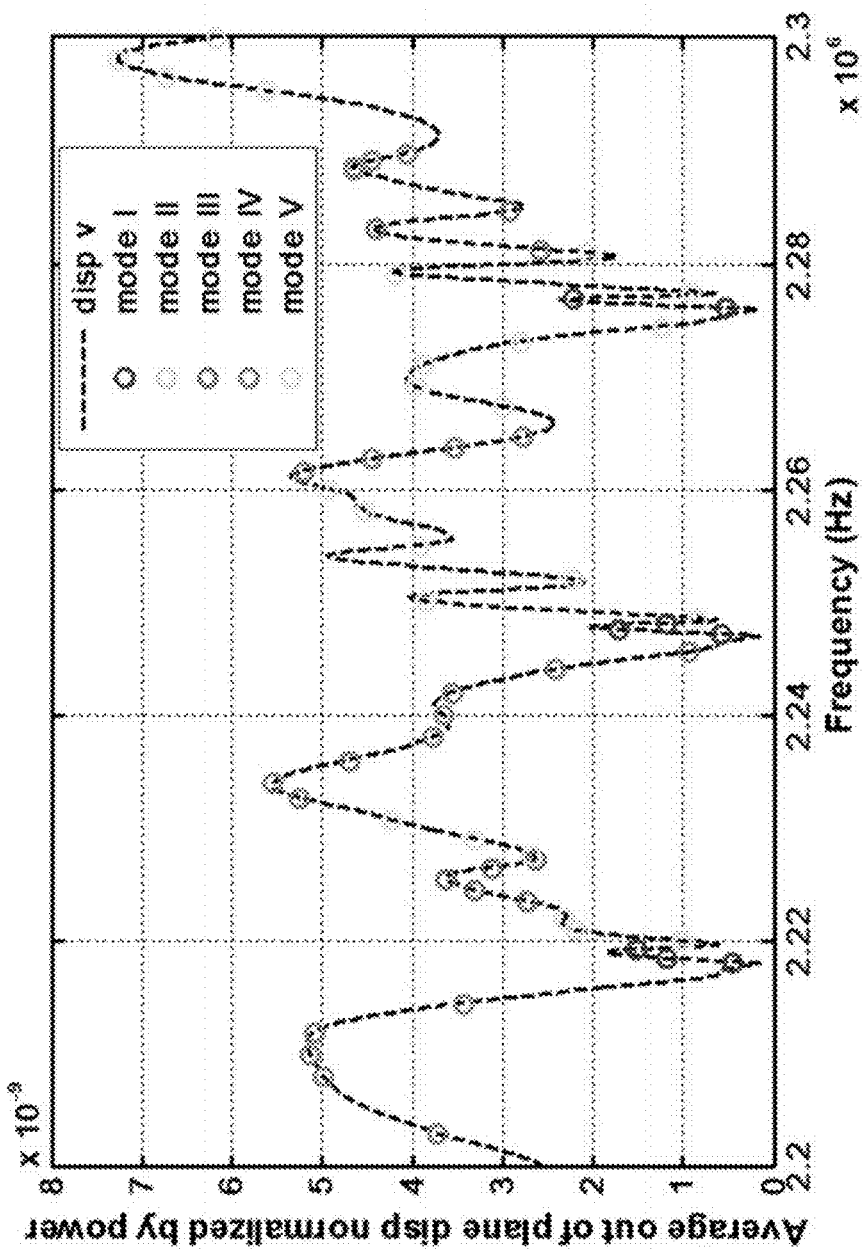
FIG. 23 is a graph illustrating displacement normalized by power.
Figure 24:
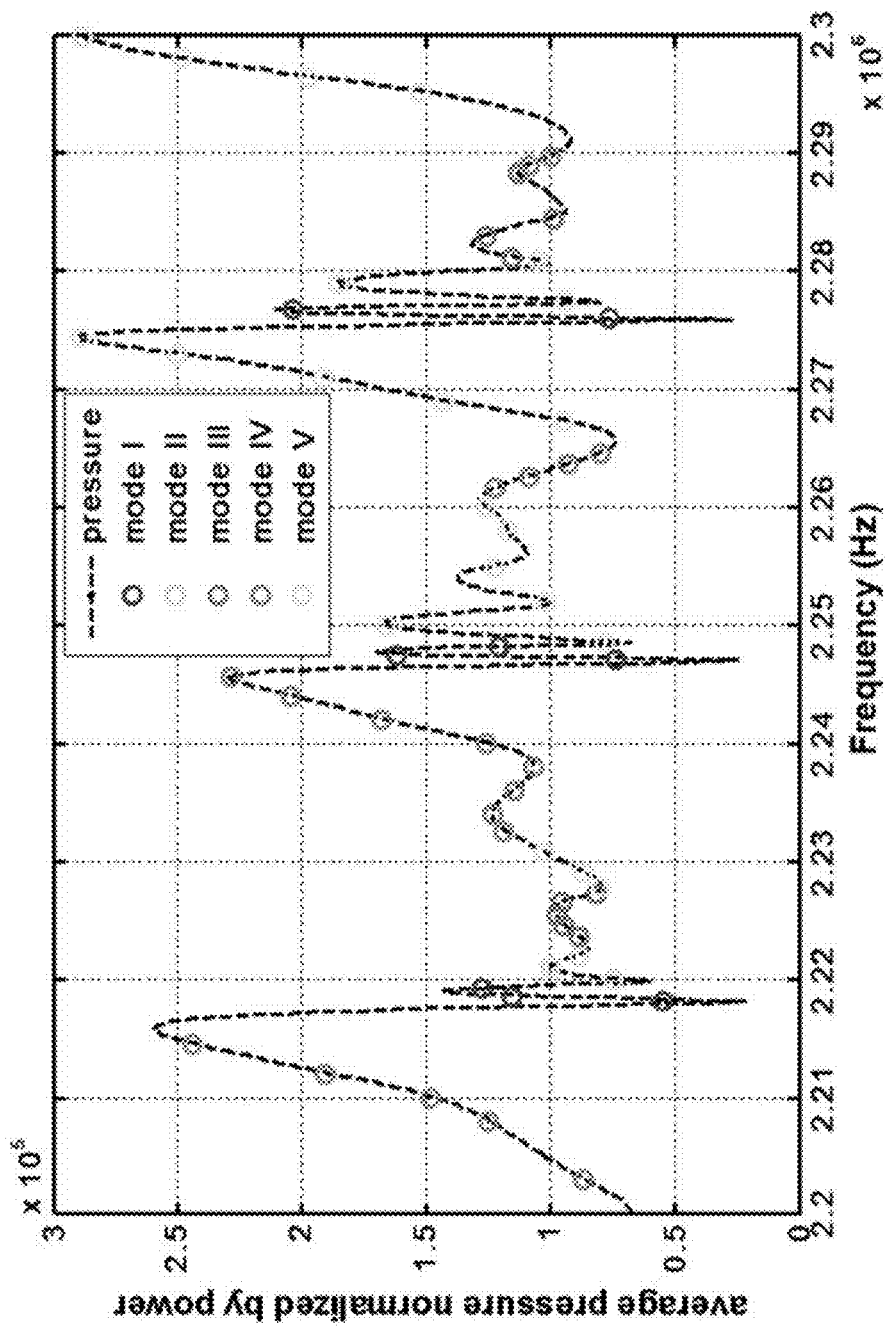
FIG. 24 is a graph illustrating average pressure normalized by power.

FIG. 23 is a graph illustrating displacement normalized by power and FIG. 24 is a graph illustrating average pressure normalized by power. Power considerations are important in most implementations, for example, a 200 Watt driver driving complex loads that vary widely in the range of voltage and current at RF frequencies places significant demands on the driver. Power can thus be controlled for multimode operation. When the operating parameters like displacement and average pressure are normalized with respect to power, it is useful to understand the best frequency for operation for a given power level. For example, the control method may seek to operate at peak pressure in multimode at the lowest useful power setting. Given the graph in FIG. 24, such a control may be difficult without relatively precise frequency control, since peak pressure in mode V is very close in frequency to a pressure minima and operation in mode I.

Figure 25:
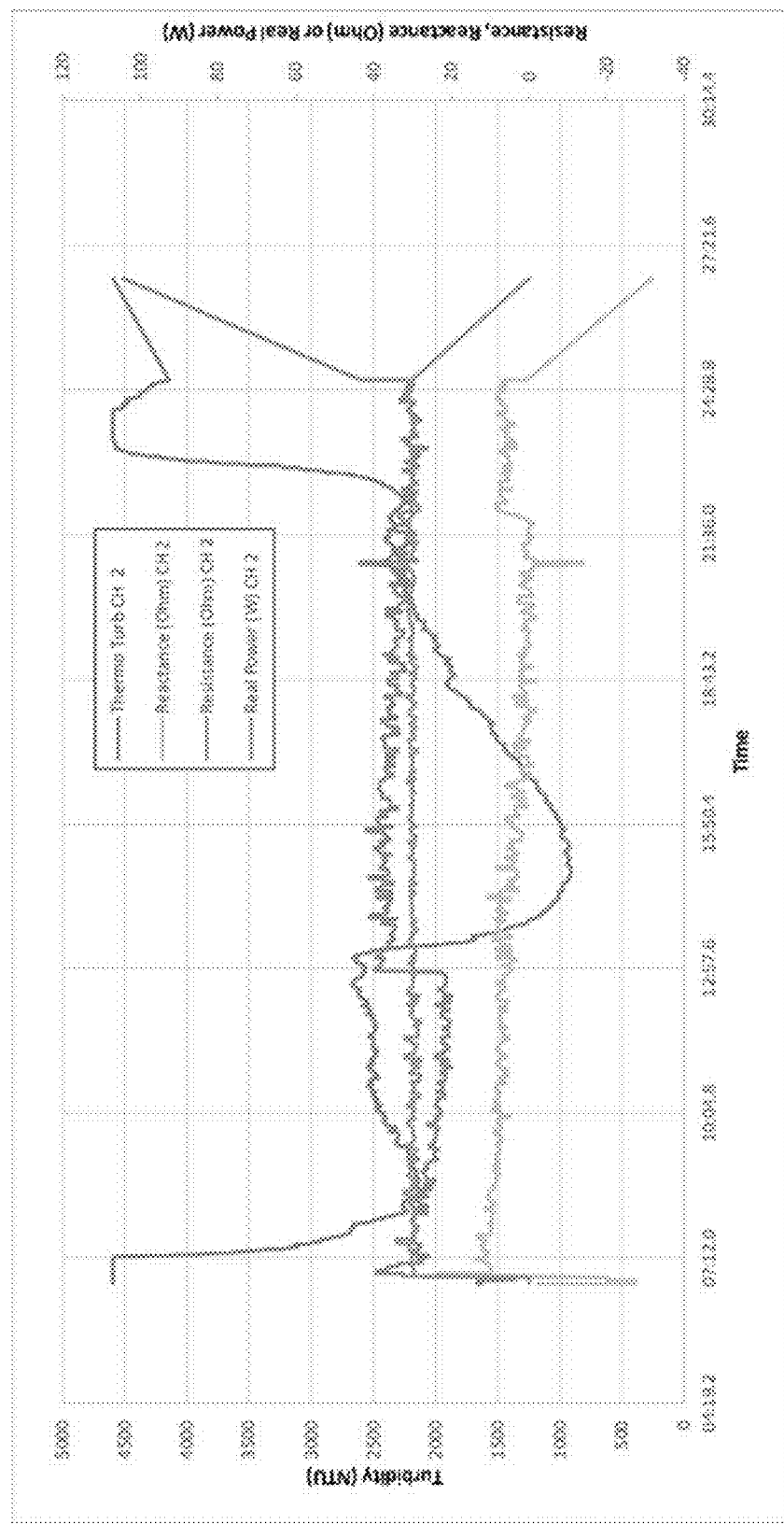
FIG. 25 is a graph illustrating operation with a planar wave at zero phase.
Figure 26:
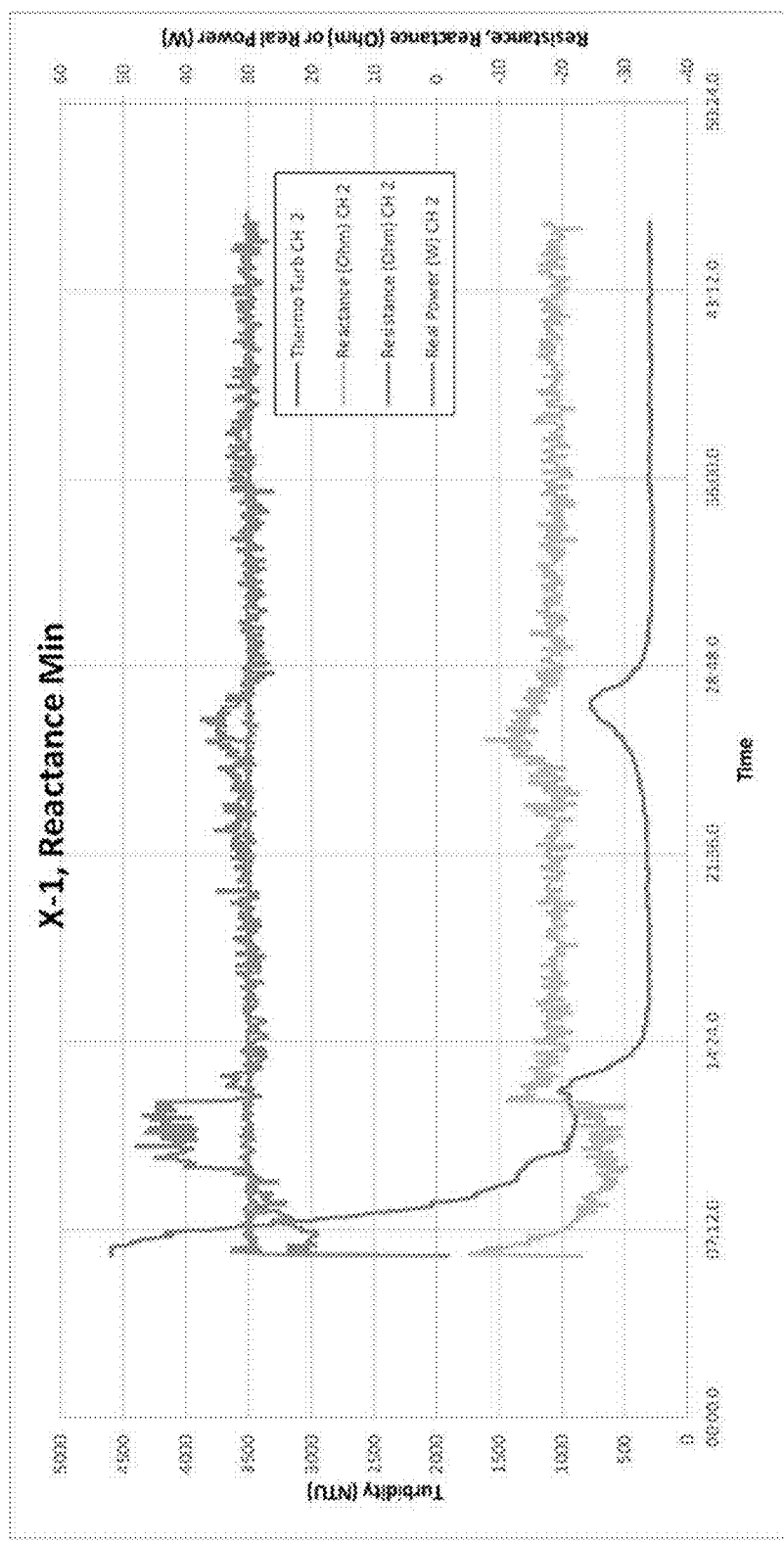
FIG. 26 is a graph illustrating multimode operation at minimum reactance.
Figure 27:
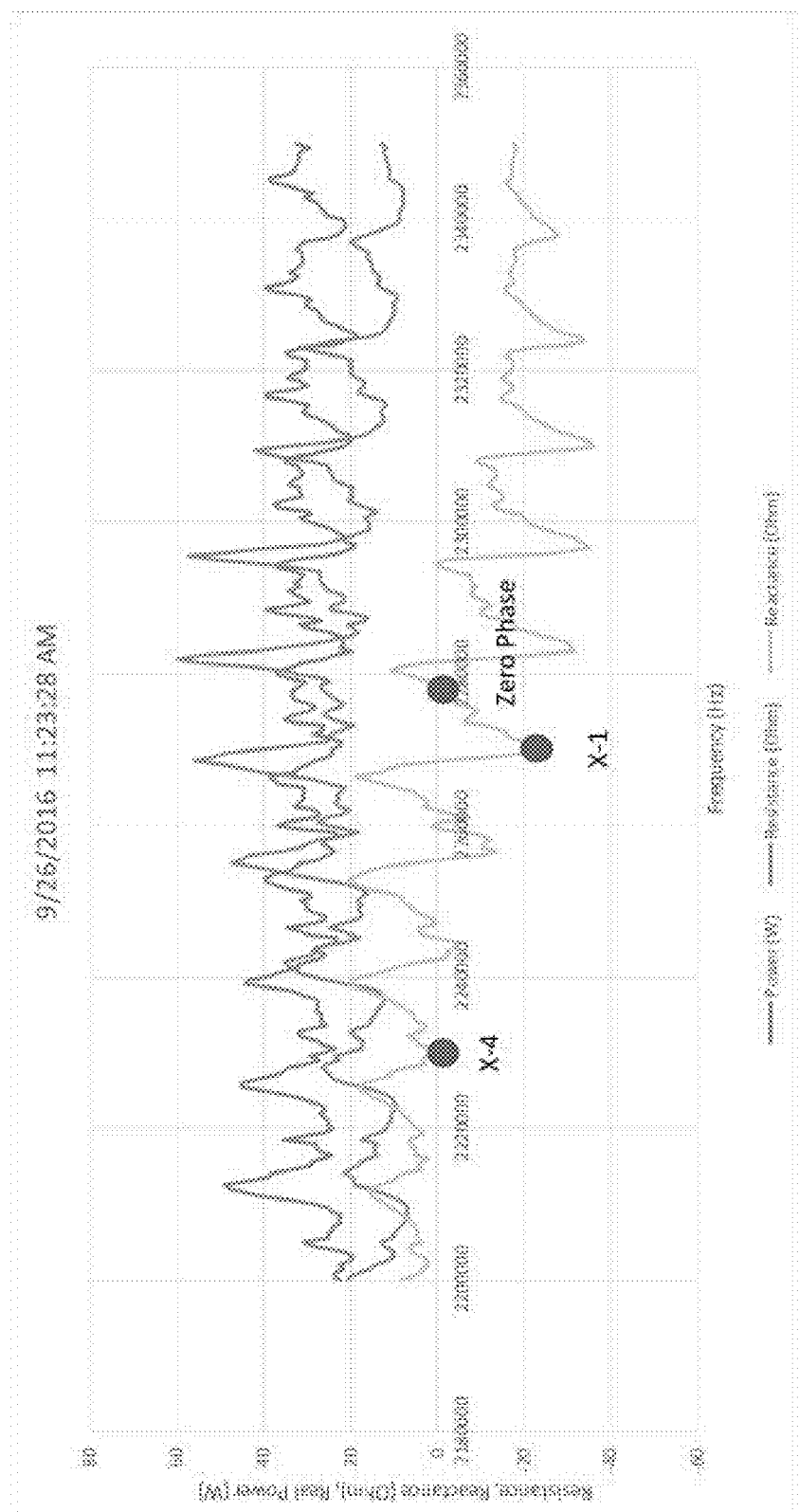
FIG. 27 is a graph illustrating resistance, reactance and real power versus frequency.

FIG. 25 is a graph illustrating operation with a planar wave at zero phase. FIG. 26 is a graph illustrating multimode operation at minimum reactance. FIG. 27 is a graph illustrating resistance, reactance and real power versus frequency. The performance illustrated in FIG. 25 is fairly poor, with a minimum turbidity of approximately 1000, and typical turbidity performance being much higher. The performance illustrated in FIG. 25 is illustrated in FIG. 27 and zero phase. The acoustic transducer in this case is producing a planar mode acoustic standing wave, which can be envisioned as piston operation.

Figure 28:
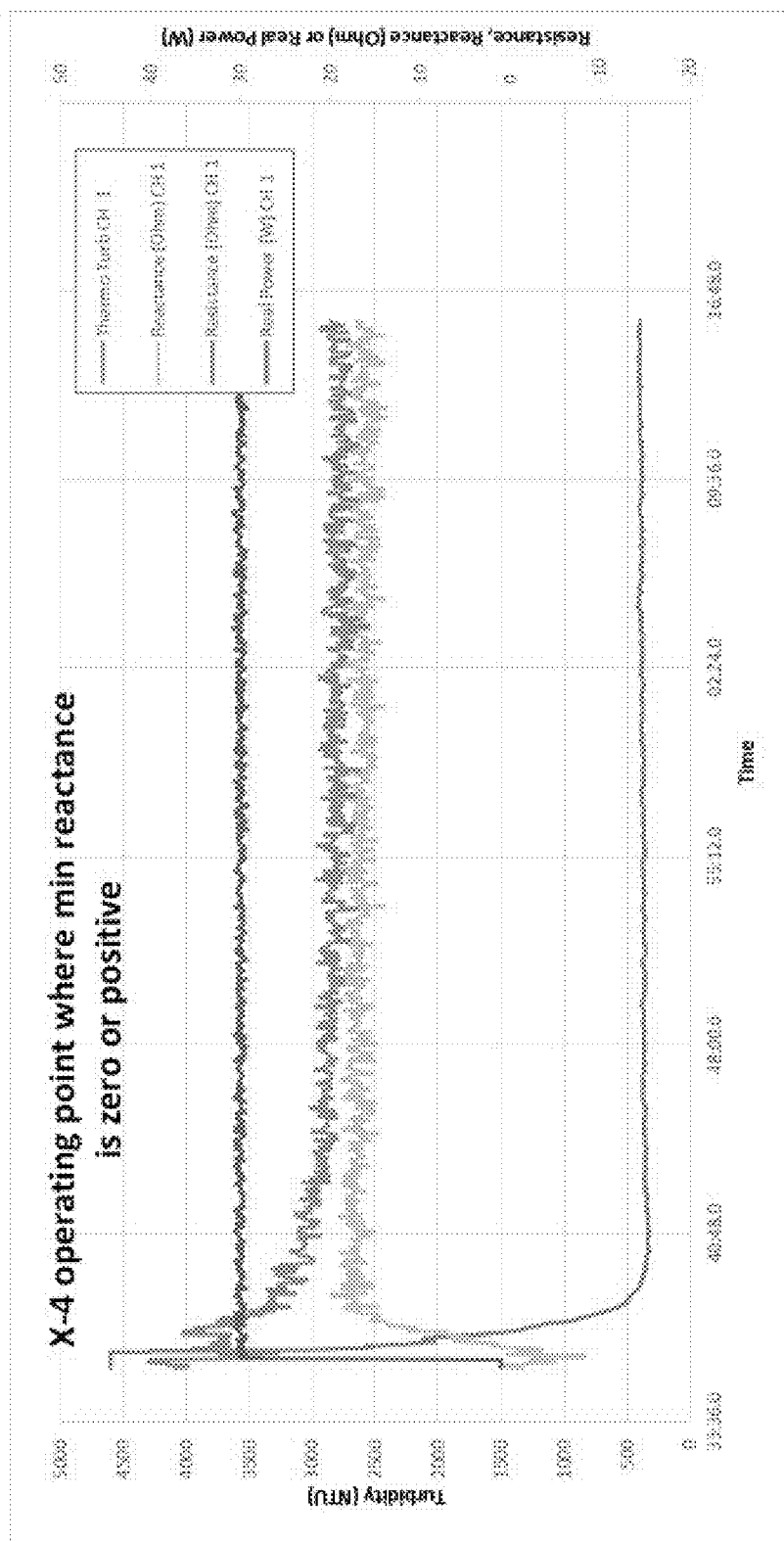
FIG. 28 is a graph illustrating multimode operation at minimum reactance.

The turbidity performance in FIG. 26 is a significant increase over that illustrated in FIG. 25, with minimum turbidity being often less than 500. The acoustic transducer in this case is operated at a reactance minimum, illustrated in the graph of FIG. 27 at point X-1. Point X-1 represents multimode operation, which can produce axial and lateral forces on particles in the fluid through which the acoustic standing wave passes. Thus, providing a control technique for operating the acoustic transducer at a reactance minimum can attain desired performance. The desired performance can be attained even at zero phase when operating in multimode, as illustrated with point X-4 in FIG. 27. Point X-4 is a reactance minimum with zero phase, which can achieve desired performance due to multimode operation, unlike the zero-phase planar wave operation. The use of X-4 as an operating point with minimum reactance is illustrated in FIG. 28. As can be seen from the figure, the X-4 operating point provides even better results than the X-1 operating point, even though the X-4 operating point is at about the same level of reactance as the zero phase operating point. This result shows the significant advantages in terms of performance for multimode operation at minimum reactances. These performance benefits are not obtained with zero or planar wave mode of operation for the transducer.

Figure 29:
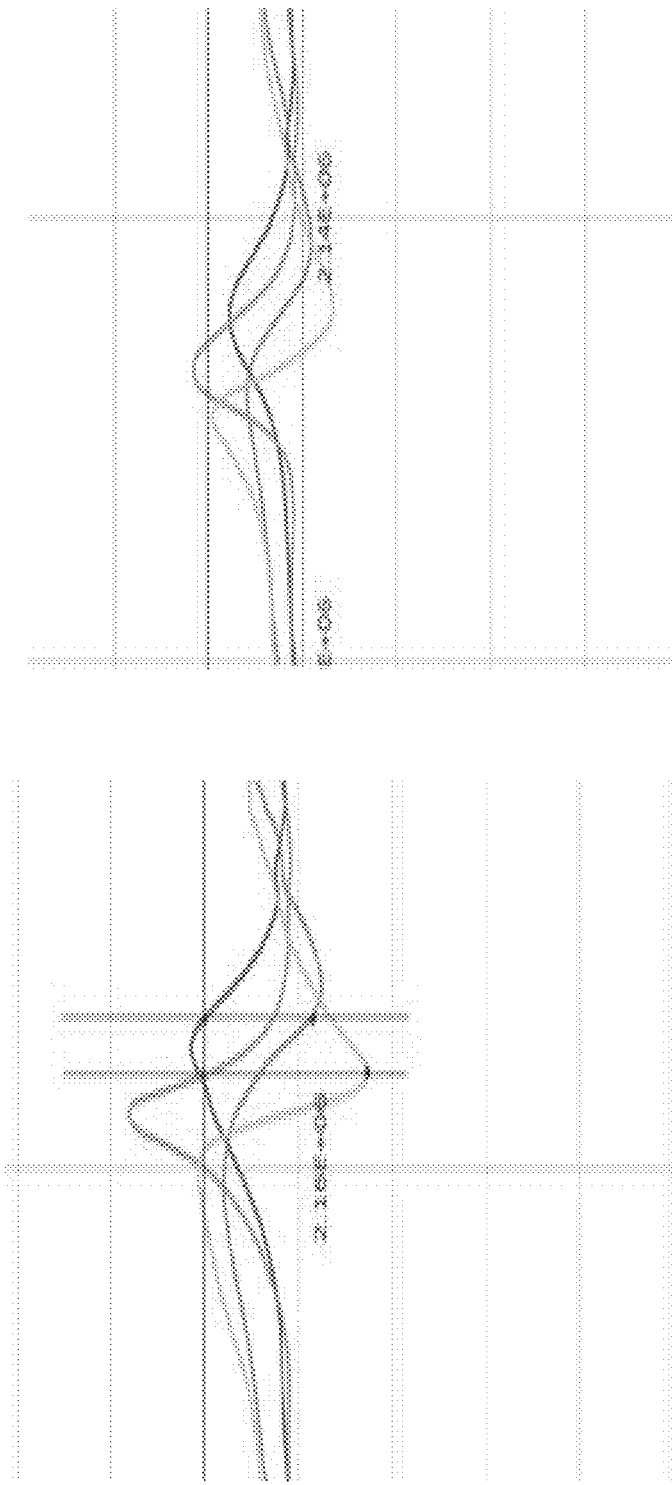
FIG. 29 is a graphic representation of resistance tracking including Rmax and a loss of tracking of the acoustic standing wave when processing a primary fluid and a secondary fluid or particulates through the acoustic standing wave.

FIG. 29 shows two graphs illustrating a resistance tracking method. The graph on the left shows resistance tracking after locating Xmin. If the tracking method is based on resistance after finding Xmin, the system can drift during operation, placing the control loop in a potential unstable condition, as illustrated with the graph on the right.

Dynamic tracking of the multidimensional acoustic wave may also be done through other minimum and maximum parameters. These include maximum and minimum resistance (Rmax or Rmin), maximum and minimum inductance (Lmax or Lmin) of the acoustic system and maximum reactance (Xmax). The key point of the algorithm for tracking being that the acoustic standing wave, such as a multidimensional acoustic standing wave, is dynamically monitored and the feedback from the changes in the various parameters of the acoustic standing wave are compensated for by the electronics to maintain the desired process capabilities of the acoustic standing wave such as trapping, clustering, segmenting or otherwise processing secondary and tertiary fluids and particles within a primary fluid.

An example method for automatically controlling the acoustophoresis process can be implemented on the basis of tightly tracking the real-power level delivered to the transducer while simultaneously tightly tracking a specific reactance location on the reactance data plot over one chamber resonance span. The reactance and power levels are extracted from the voltage and current signals on the piezoelectric element and provides constant feedback for the controls tuning process. This tuning process consists of adjusting the gain of the output driver amplifier in to deliver a constant real-power level to the piezoelectric element and by adjusting the frequency of the drive signal in order to track a desired reactance location on the reactance curve.

The method uses a control technique that continuously performs frequency mini-sweeps (a small local frequency sweep) to track a multi-modal trapping pattern relative to the minimum reactance. This minimum reactance lies within a single selected chamber resonance and is calculated from the sensed voltage and current at the transducer. In one example implementation, the method uses a reduced number of frequency steps to reduce or minimize the frequency span over which the power will be spread. Another example implementation may use as small a frequency band as possible to perform the desired control. A frequency sweep rate that is much higher than the system dynamics may be used. Such a high sweep rate permits the control to respond more rapidly than the physical dynamics of the loaded resonance chamber, so that Xmin tracking can be more accurate and consistent. For example, a control rate of from about 3 kHz to about 300 kHz may be used.

At each frequency step in the mini-sweep a new reactance value is calculated based on newly acquired voltage and current data. This new reactance value is then compared to a currently stored previous minimum reactance value and replaces that value if a lower, or more negative reactance value is found. Upon completion of the frequency sweep, this method has the effect of locating the minimum reactance value across the entire mini-sweep. The final step of the algorithm sets/parks the output frequency at this newly located reactance minimum, plus a frequency offset if desired. This process is repeated at a rate fast enough to track any physical changes in the conditions within the acoustophoresis process taking place inside the resonance chamber.

Figure 35:
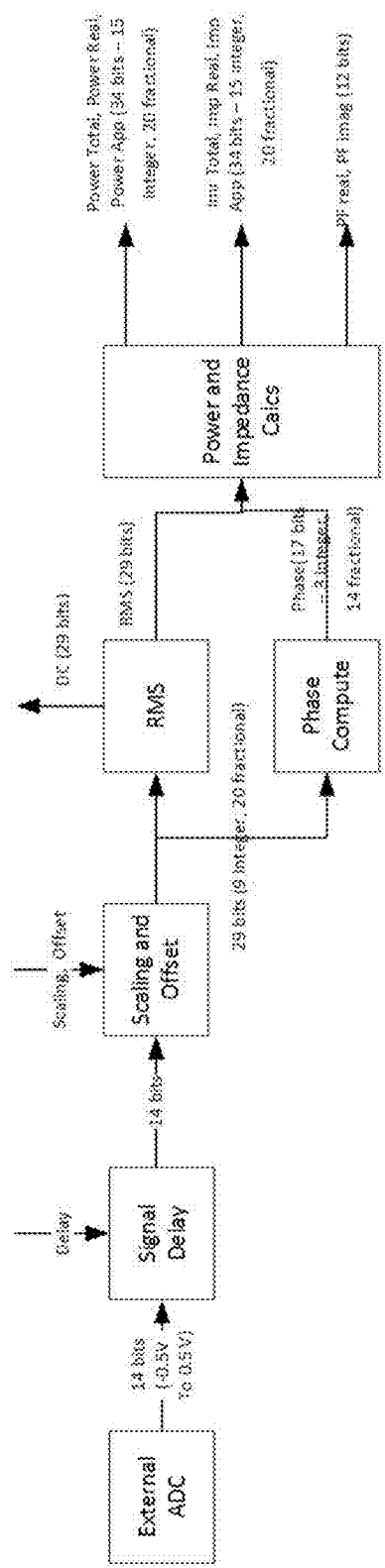
FIG. 35 is a diagram of the control system.
Figure 36:
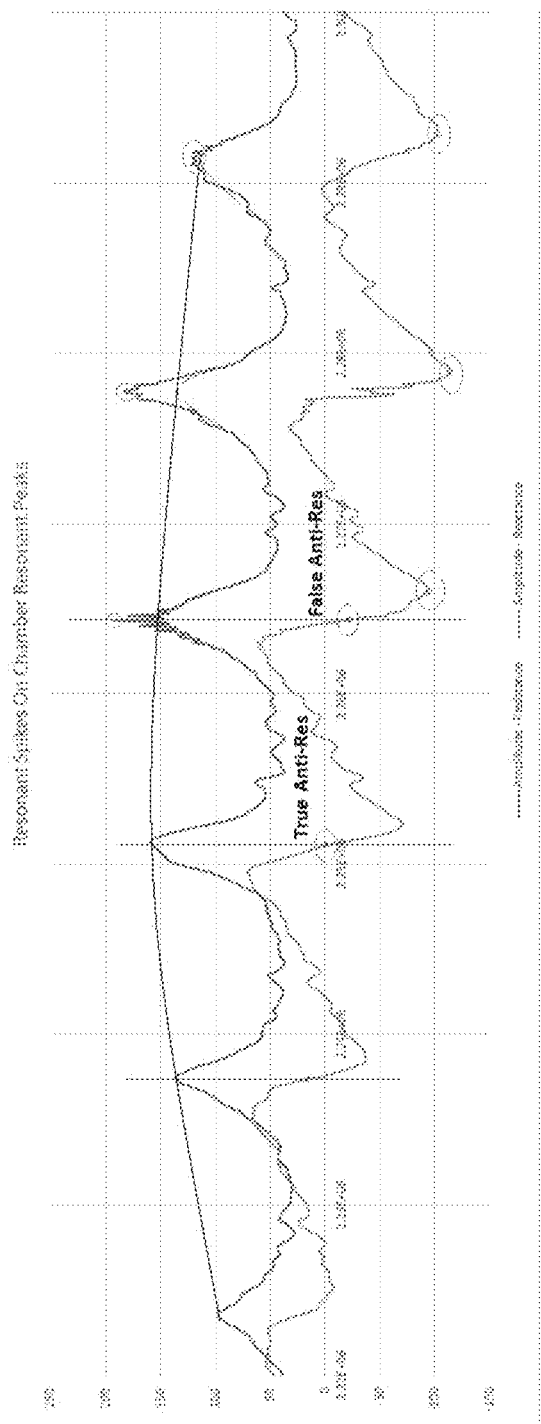
FIG. 36 is a graph of resistance and reactance versus frequency for global frequency sweep from about 2.22 MHz to about 2.30 MHz.

The control process implements a number of steps to closely track a desired Xmin point. Referring to FIG. 35, a control system for computing various parameters used to track Xmin is illustrated. Referring to FIG. 36, a global frequency sweep is performed to locate an anti-resonance point in the resonance chamber response. The frequency of the anti-resonance point is saved later reference. The anti-resonance frequency is where a resistance maximum peak lines up with a point where the reactance crosses zero, which may occur at a single point in the frequency response. The zero crossings of reactance are the eigenvalues of the system. By monitoring the resistance and the reactance as frequency is varied, the anti-resonance can be determined using these criteria. In some examples, the frequency scan, which may be a global frequency scan, is from 2.22 MHz to 2.26 MHz, which covers a number of semi-periodic peaks and valleys for both resistance and reactance. In other examples, the scan range is from 0.5 MHz to 1.5 MHz or from 2 MHz to 2.5 MHz, or portions of those ranges. The scan may have frequency steps in a size of about 2 kHz, although any other suitable step size may be used. In some examples, the system attains high efficiency when the current peaks. Current can be monitored while frequency is varied to identify peak current.

Figure 37:
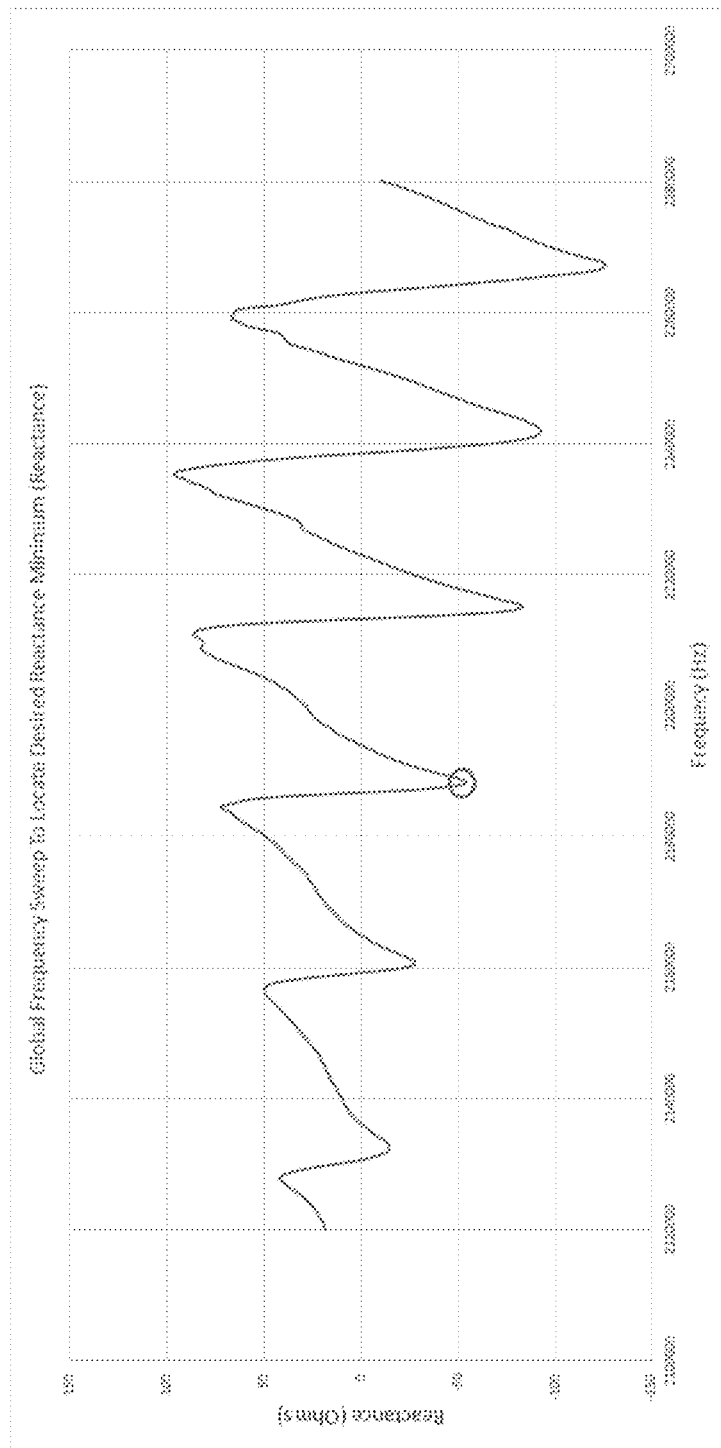
FIG. 37 is a graph of reactance versus frequency for a global frequency sweep from about 2.10 MHz to about 2.30 MHz.

The frequency scan can be done in steps or continuously. The rate, or step size for the frequency increase can be specified by a user input and/or can be determined based on several parameters. For example, if the acoustics path-length is known, it can be provided to the system to permit calculations to be performed to determine resonance spacing for a standing wave. The resonance spacing can be used to determine frequency setpoints to operate at a resonance location, which can be inspected with a finer frequency gradation to locate minima and/or maxima for resistance and reactance. For example, a frequency resolution as small as 23 mHz (milli Hertz) may be obtained for the control discussed herein. FIG. 37 is a graph showing the results of a global frequency sweep to reactance minima.

Figure 38:
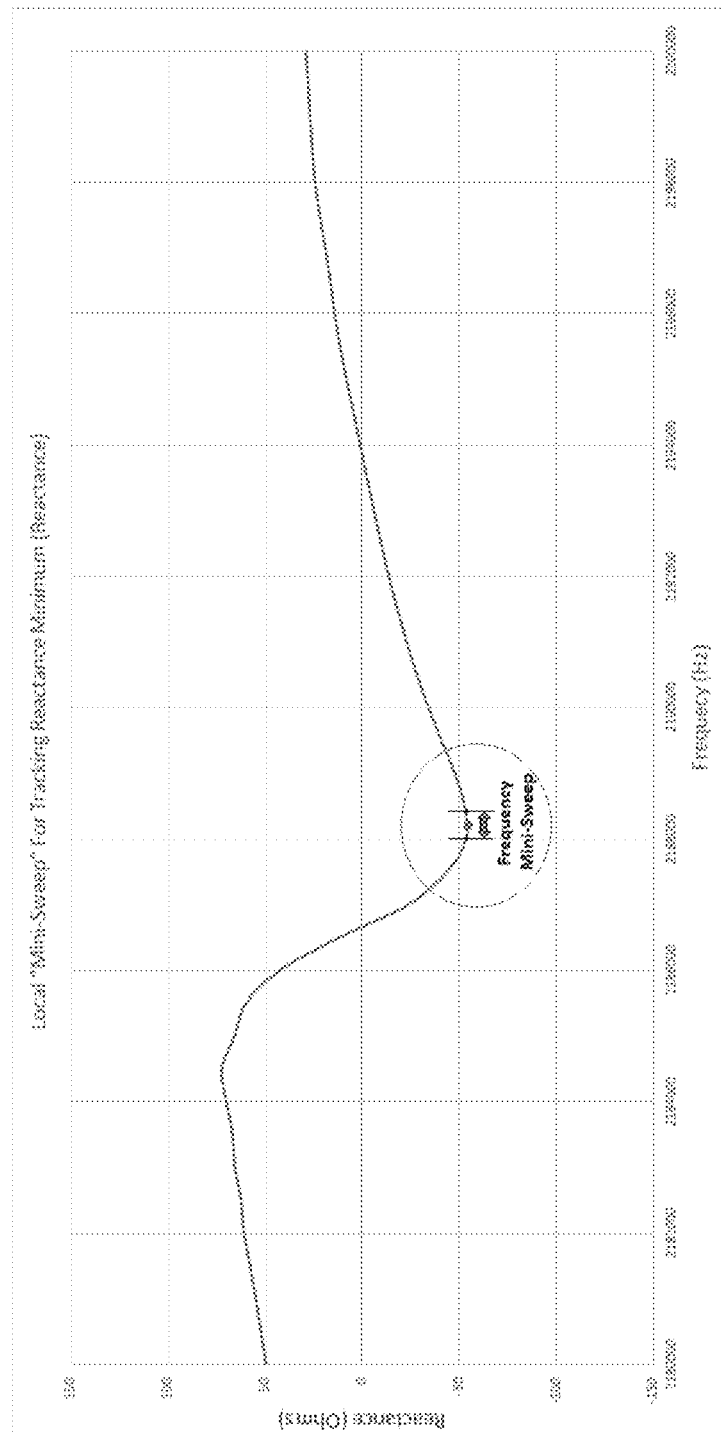
FIG. 38 is a graph of reactance versus frequency for a mini-sweep from about 2.18 MHz to about 2.20 MHz.
Figure 39:
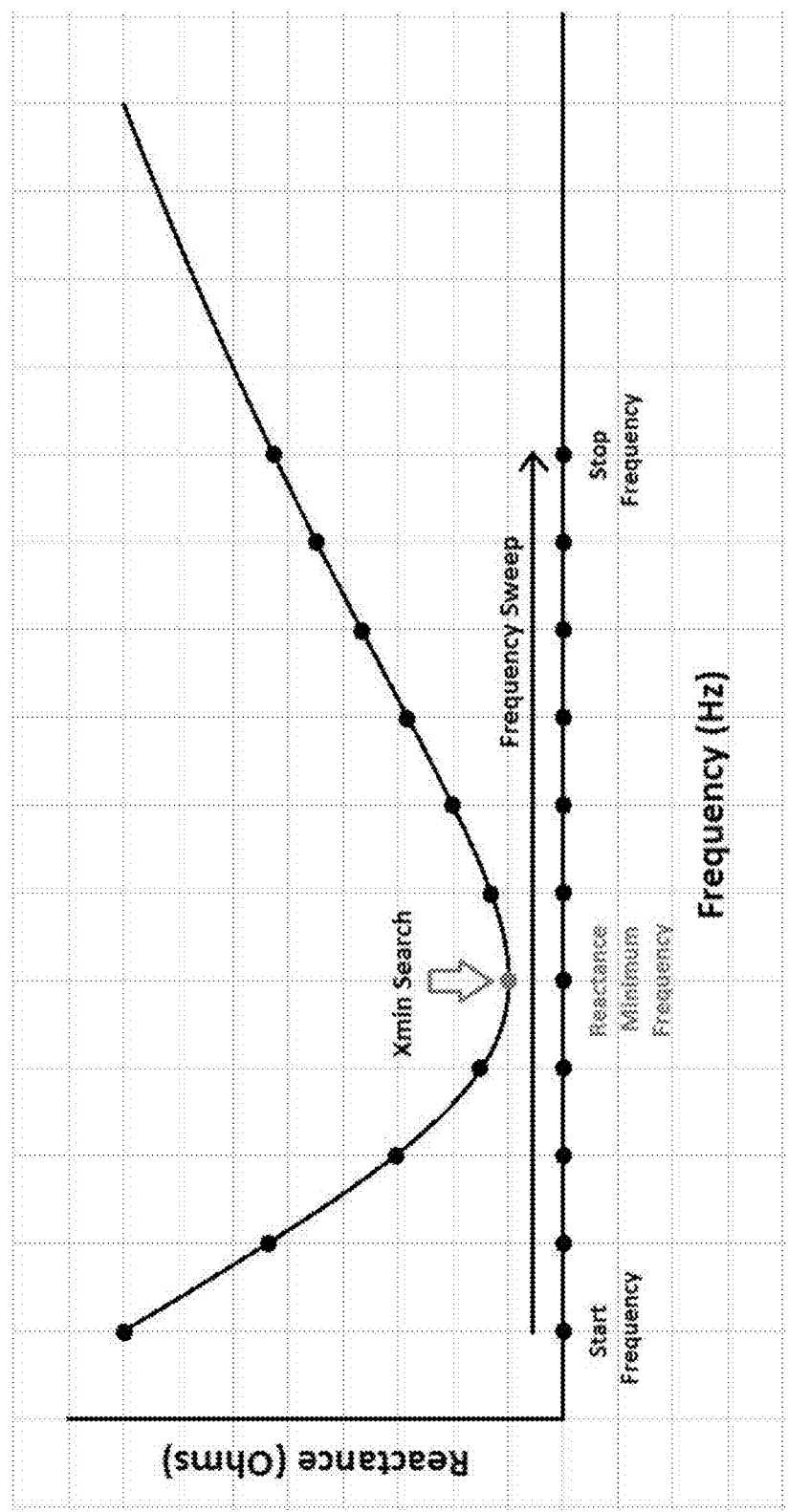
FIG. 39 is a graph of reactance versus frequency for a control technique.

The identified minima for the system reactance are then further inspected in a smaller frequency interval to obtain a local minimum reactance, which can be used as an initial operating setpoint. The smaller frequency sweep, or mini-sweep, produces a local minimum reactance value and associated frequency, which can be used to initialize Xmin tracking. The localized mini-sweep and resulting minimum reactance and Xmin frequency are illustrated in FIGS. 38 and 39.

The process uses the initial setpoint as the starting point for conducting continuous mini-sweeps about the minimum reactance location. Parameters for the mini-sweep are established, such as a sweep step size, sweep radius and/or method type. The lower and upper bounds of the sweep range are identified. The sweep begins at the lower bound and measures voltage and current on the transducer to determine resistance and reactance at that frequency. The frequency is changed in accordance with the step size, and the measures are again taken. As the sweep continues, the value of the reactance at each frequency is determined and may be stored or compared to a stored value. The least reactance value is identified in this sweep, and becomes the new Xmin. The new Xmin can be used to determine new boundaries for the next sweep. For example, the new Xmin frequency can be set to be a center frequency for the next sweep. The boundaries of the sweep are determined by the sweep radius with the new Xmin in the center of the radius.

The mini-sweep can be conducted continuously to dynamically track Xmin. The selected Xmin operating point can be tracked according to a number of different methods. As the minimum reactance shifts due to operational factors, discussed above, the Xmin tracking method continues to locate the minimum using the mini-sweep technique. As the minimum reactance is located, the method sets new mini-sweep parameters to, among other things, center the frequency of the new minimum reactance within the mini-sweep range. This tracking technique continuously locates a new reactance minimum frequency within a relatively small window of frequencies, which increases speed and accuracy of the method. The adjustment of the center frequency of the window permits the window boundary frequencies to be determined for following iterations of the mini-sweep.

The mini-sweep process and frequency tracking and adjustment is continuously repeated to continually locate the reactance minimum as the physical dynamics of the acoustic system change. The rate of repetition of the mini-sweep at a speed that is greater than physical system phenomena adds to the continued tracking accuracy, and contributes to improved or optimized operation at a desired dynamic setpoint.

This control system automatically sets the step size or gain of the proportional tracking algorithm. When a new reactance minimum location is found within a mini-sweep, that new frequency is used as the setpoint, e.g., the control jumps to that frequency location, regardless of the size of the change in frequency. As long as the sweep is wide enough to contain any changes in minimum reactance, the method will track the desired setpoint of minimum reactance. This technique has a number of advantages over a proportional controller, for instance because a proportional gain need not be tuned. The algorithm dynamically tunes itself regardless of the conditions in the acoustic chamber. The frequency step size and the number of frequency steps are chosen based on the system characteristics such that any changes in the acoustophoresis process will be detected by changes in the frequency and minimum reactance location within one frequency sweep.

Figure 30:
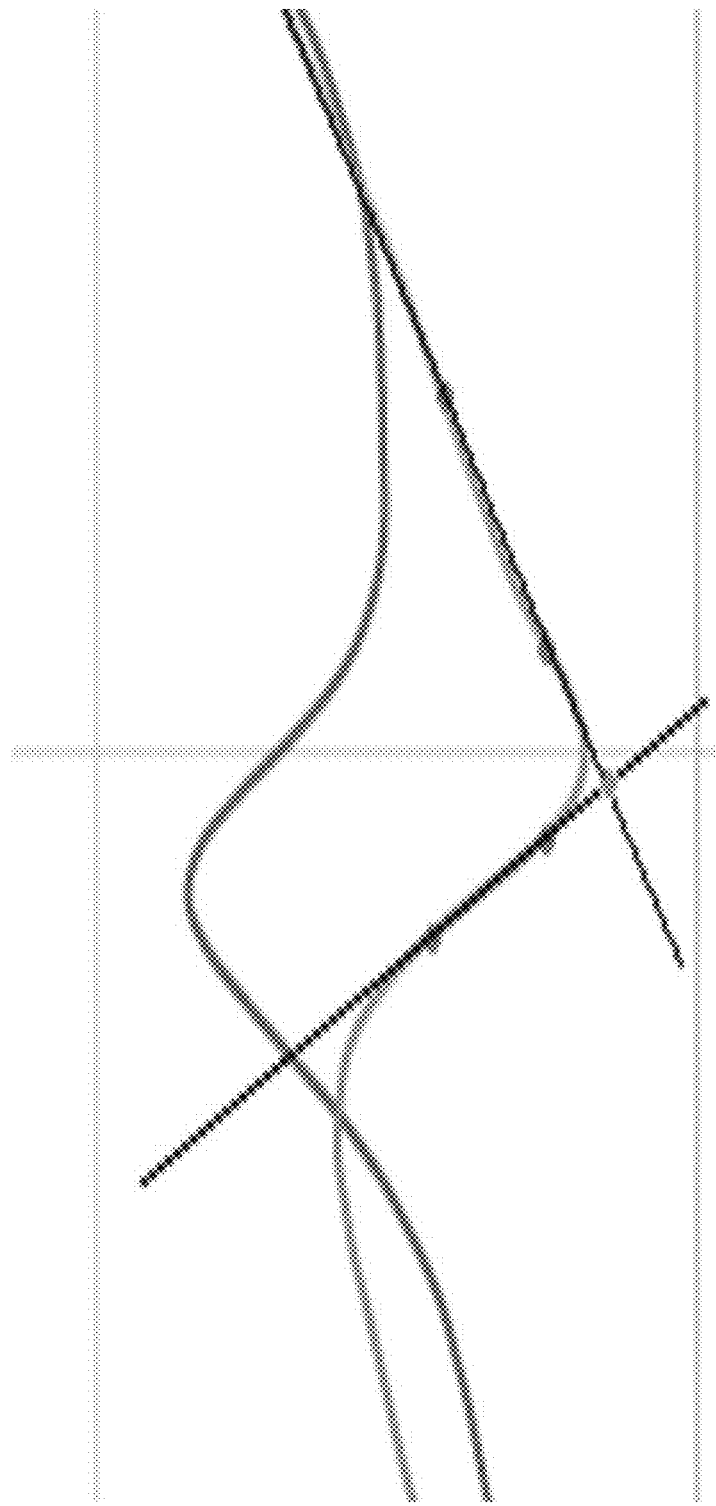
FIG. 30 is a depiction of a frequency sweep about a reactance minimum defined a new reactance minimum utilizing four points on a curve in the new minimum reactance frequency.

FIG. 30 illustrates a technique for locating Xmin using a mini-sweep method. An initial Xmin is located as discussed above. Four points on the reactance curve are chosen to represent lines on either side of the initial Xmin value. The equations for the lines can be solved to identify their intersection. This intersection is used as the new Xmin value. This technique is very fast as only four points are used, and may be sufficiently accurate for a number of applications.

Figure 31:
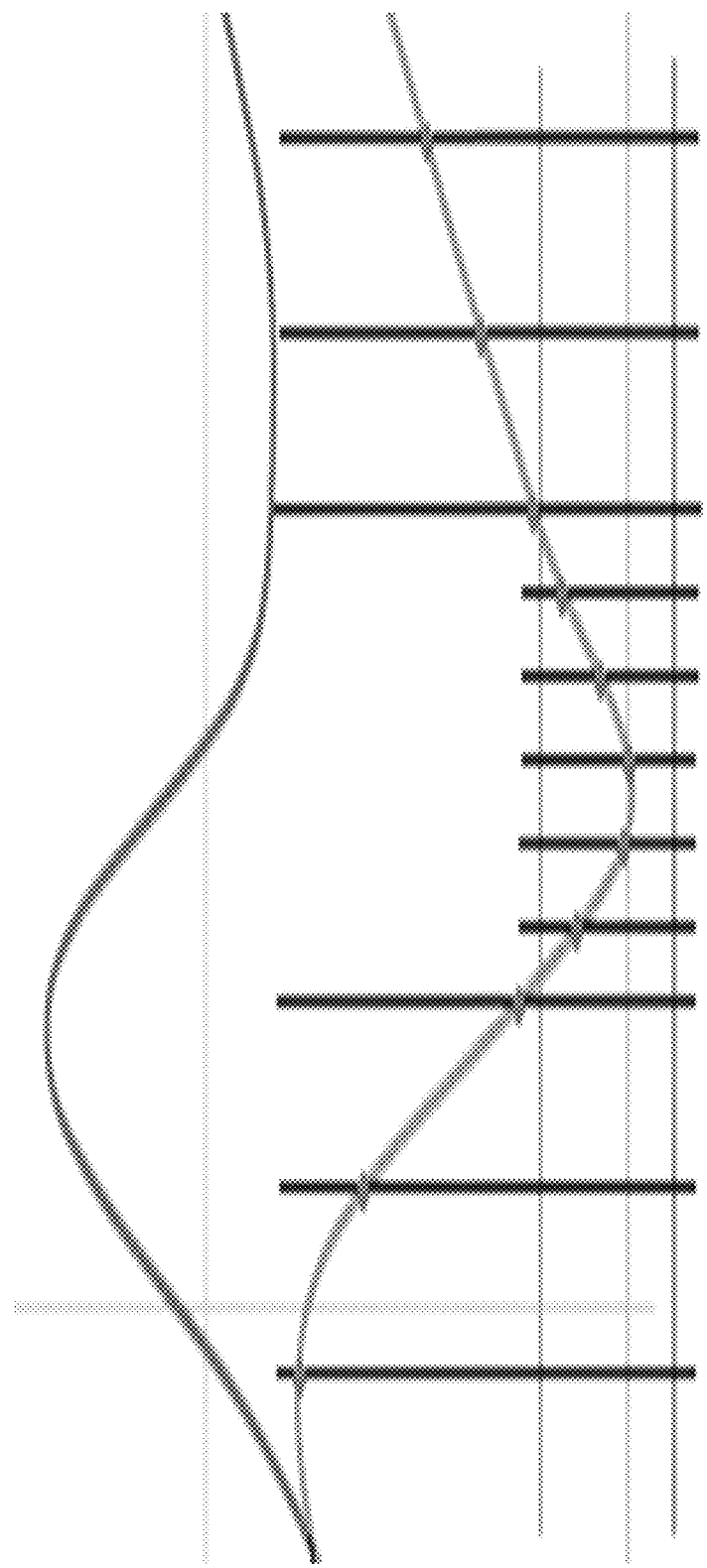
FIG. 31 is a depiction of the interrogation of the minimum reactance curve with a two-step size interrogation of the points on the curve.

FIG. 31 illustrates an Xmin mini-sweep process with two different step sizes to manage Xmin tracking. A larger step size may be used outside a given range of the identified minimum reactance (Xmin), which may assist in closing to the desired operating point faster. The number of frequency steps may be reduced. A threshold may be used to determine which step size to use. For example, the equation X−Xminprev>Threshold can be evaluated, and a larger step size can be used if the expression is true, and a smaller step size if the expression is false. A smaller step size may be used in a given range around the minimum reactance so that finer changes in control frequency may be obtained.

Figure 32:
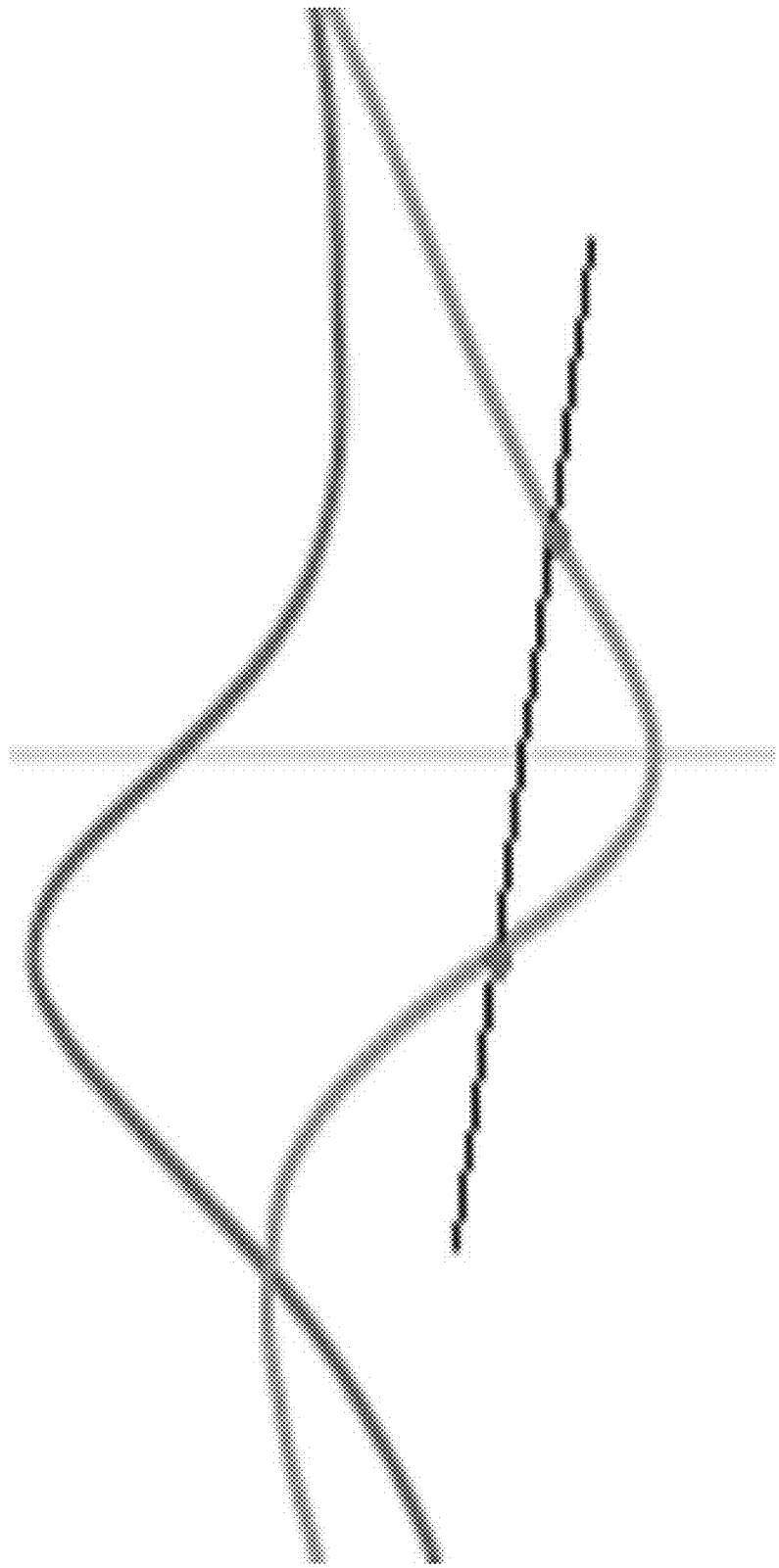
FIG. 32 is a pictorial of finding two points on the reactance curve in order to find Xmin or the minimum reactance.

FIG. 32 illustrates another method for mini-sweep tracking of Xmin. This approach automatically switches the gains in a PI loop to rapidly converge to Xmin. Positive PI gains are additive—frequency goes up to increase resistance—and negative PI gains are subtractive—frequency goes down to increase resistance. Two points about Xmin are scanned and the slope of the line formed by the two points gives a magnitude, while the sign of the slope sets the gain polarity, which can be used to automatically set the PI gain polarities. The equation Slope=(X2−X1)/(F1−F2) may be used to determine slope magnitude and polarity. This technique can be used to rapidly locate Xmin, using just two points and a PI loop. The magnitude and polarity are generated automatically and immediately usable, adding to the speed of this method.

Figure 33:
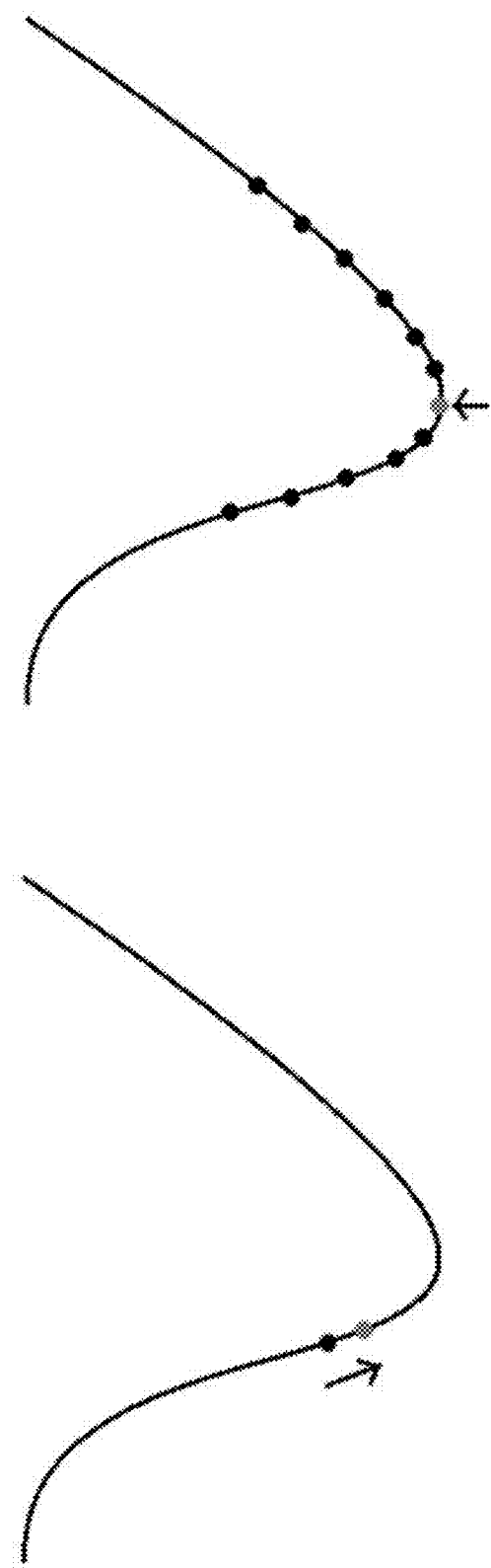
FIG. 33 is a depiction of two reactance curves and different tracking modes.

FIG. 33 illustrates an iterative method for tracking Xmin. Two points on the reactance curve near Xmin are evaluated for reactance magnitude. The difference between the points are provided to a PI loop to magnify the difference when it is larger, e.g., when the slope of the curve is steeper. The output of the PI loop is used to adjust the frequency step to increase the step to seek more rapid convergence when there is a large difference between the points. The PI loop provides a smaller step as the frequency point approaches Xmin, since the differences between the reactance magnitude at two points near the bottom of the curve is smaller. This approach helps to obtain rapid convergence to Xmin, although a number of iterations may sometimes be used.

Figure 34:
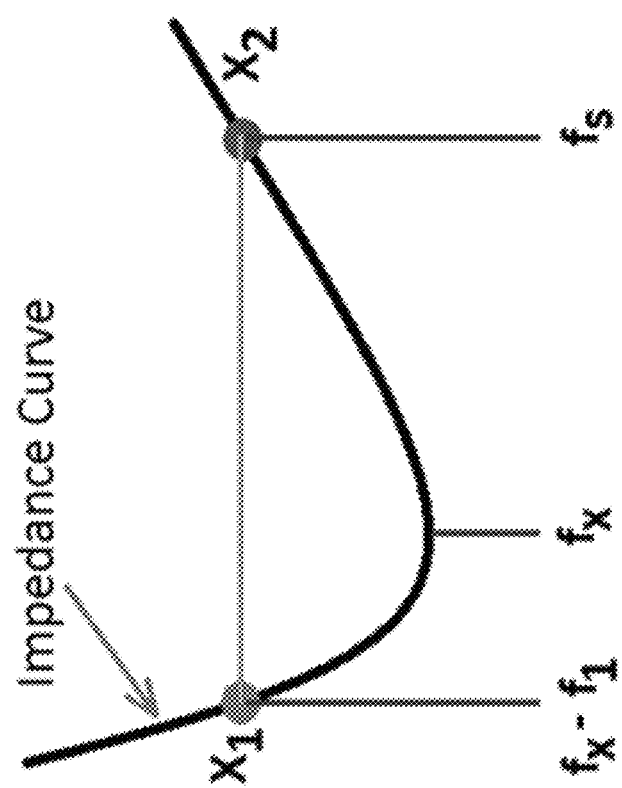
FIG. 34 is a graph of a reactance curve.

FIG. 34 shows an example tracking method based on tracking the change in slope of a line tangent to the minimum point of a reactance curve. Since trying to track adjacent points at the bottom of such a curve can be extremely inaccurate, a virtual tangent line is created which is parallel to the tangent line at the base of the curve. This approach increases resolution of slope changes under the assumption that the two lines remain essentially parallel as the curve changes amplitude and frequency location.

The tracking algorithm has as its input the frequency, fx, at which a reactance minimum, Xmin, has been found within a certain cavity resonance interval. An incremental frequency, f1, is chosen based on the level of tracking resolution desired. The value of the reactance, X1, is found at the starting frequency, fx−f1. A search is initiated that incrementally advances the frequency from the start frequency searching for a value of X2 which is equal to X1 to within some error bound. The frequency at which X2 is found, fs, is converted to a frequency relative to fx, or f2=fs−fx. The two relative frequencies, f1 and f2, are stored for future use in tracking.

The tracking process is iterative. Given the current value of fx, the algorithm finds the value of the reactance at fx−f1, call that X1, and fx+f2, call that X2. If X2 is greater than X1 then decrement the value of fx. If X2 is less than X1 then increment the value of fx. If X1 and X2 are essentially the same, do nothing. The increment applied to fx is determined from tracking speed considerations. The bigger the increment, the bigger the frequency jumps in finding where the Xmin moved to. Note that this tracking algorithm does not rely on actual reactance values but only on relative ones since in the acoustic system this has been designed for, the actual values are dynamic but the reactance shape over a band of frequencies is relatively constant. Continuous tracking is achieved by repeating the above steps of finding X1 and X2 about the current fx using the fixed f1 and f2 values and determining the 'tilt' of X2 relative to X1.

In addition, different tracking techniques may be used with different parameters, such as by tracking a resistance (Rmax) associated with the desired minimum reactance. For example, resistance or a multimode frequency of interest may be tracked, or any other parameters that provide suitable performance.

Referring to FIG. 39, the speed of the process for the frequency sweeping or scanning can be related to the system and/or the trapping or clustering of the material that is retained or that exits the acoustic field or acoustic standing wave. The combination of the hardware and the processes implemented on the hardware produce the control speed that is used to obtain the tracking technique for tracking minimum reactance frequency. The averaging that takes place, explicitly and/or implicitly, e.g., via the hardware and/or software, separately or in combination, and/or system operation or system characteristics, such as natural system resonances, can be used for operating the tracking process. For example, the averaging that takes place may result in a control speed in the kilohertz range.

The tracking process adapts to the dynamics of the system, such as when material is captured in or released from the acoustic field or acoustic wave, or when the temperature of the system changes, or when other system parameters change during operation. The reactance minimum can experience a frequency shift due to a number of different system variables. The processes described herein can be used to adapt to those changes and maintain a high efficiency and high level of performance, even with significant changes in system dynamics.

Moreover, the processes and/or algorithms discussed herein can be provided with ranges for various parameters, which allows a choice or selection of the parameter value over a range. For example, clock speeds, data acquisition rates, control rates, mini-sweep resolutions, and/or any other useful parameters may have a range of values that permit a user to provide a setpoint, or that permit automatic adjustment based on feedback or other set or measured parameters.

The systems and methods discussed herein may be utilized on other forms of acoustic waves. For example, the techniques discussed herein may be employed with an angled acoustic standing wave, the edge effect achieved in an acoustic standing wave where the edge of the acoustic standing wave repels particles in a host fluid while allowing the host fluid and other moieties to flow through the acoustic standing wave and traveling waves that are utilized by themselves or where at least two traveling waves are utilized to form an acoustic standing wave.

The techniques discussed herein may be utilized in conjunction with a cell concentrate and wash system, an affinity binding system and/or other acoustic configurations for cellular and biomaterial processing. Other applications or implementations include the transduction and transfection of cells, such as T cells, with viruses and nucleic acids respectively.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the spirit of the disclosure. For example, the above elements may be components of a larger system, wherein other structures or processes may take precedence over or otherwise modify the application of the invention. Also, a number of operations may be undertaken before, during, or after the above elements are considered. Accordingly, the above description does not bound the scope of the claims.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

What is claimed is:

1. A control system, comprising:
an electronic driver for driving a load that exhibits dynamic impedance;
a controller coupled to the electronic driver and to the load for controlling a frequency of a drive signal applied to the load, the controller being configured to control the frequency of the drive signal based on impedance determined from a feedback signal from the load; and
the controller being configured to determine a frequency associated with impedance minima or maxima of the load.

2. The system of claim 1, wherein the impedance minima or maxima are reactance minima or maxima.

3. The system of claim 2, wherein controller is configured to generate a control signal to cause the electronic driver to provide the drive signal to the load at the frequency associated with a reactance minimum or maximum.

4. The system of claim 1, wherein the controller is configured to determine a reactance value for the load for at least some frequencies in a range of frequencies, such that a minimum or maximum reactance value is determined for the range of frequencies.

5. The system according to claim 4, where in the controller is configured to identify a new frequency in the range of frequencies associated with the minimum or maximum reactance value so as to track changes in the frequency at which a minimum or a maximum reactance of the load occurs.

6. The system of claim 1, wherein the load is an acoustic transducer.

7. The system of claim 1, wherein the controller is configured to determine electrical power consumed by the load based on the feedback signals.

8. The system of claim 7, wherein the controller is configured to control one or more of a voltage, a current or a frequency of the drive signal provided to the load to control electrical power consumed by the load.

9. The system of claim 1, wherein the controller is configured to decompose the feedback signal into in-phase and quadrature-phase components.

10. The system of claim 9, wherein the controller is configured to determine phase angle and reactance based on the in-phase and quadrature-phase components.

11. The system of claim 1, further comprising pipelined analog-to-digital converters for sampling voltage and current of the load.

12. The system of claim 1, wherein the controller is configured to initiate a frequency scan based on one or more of a timed interval or an event.

13. The system of claim 12, wherein the controller is configured to receive parameters of the frequency scan that include one or more of a frequency range, a frequency step size or a frequency step time interval.

14. The system of claim 1, further comprising a filter between the electronic driver and the load.

15. The system of claim 1, wherein the electronic driver further comprises a DC converter and an RF inverter.

16. The system of claim 15, further comprising a filter between the DC converter and the RF inverter.

17. A device for controlling a dynamic impedance load, comprising:
a controller for implementing a control scheme;
a power section connected to the controller for supplying power to the load; and
a feedback section interposed between the load and the controller to provide feedback to the controller for operating parameters of the load;

wherein the control scheme includes controlling power supplied to the load based on impedance determined from the feedback; and the controller being configured to determine a frequency associated with impedance minima or maxima of the load.

18. The device of claim 17, wherein the control scheme further comprises controlling a frequency of the power supplied to the load to track a minimum or maximum reactance of the load.

19. The device of claim 18, wherein the control scheme further comprises adjusting a frequency sweep range in which the minimum or maximum reactance of the load is expected.

* * * * *